(12) United States Patent
Harrington et al.

(10) Patent No.: US 10,239,913 B2
(45) Date of Patent: *Mar. 26, 2019

(54) COMPOUNDS AND METHODS INVOLVING STEROLS

(71) Applicant: Warsaw Orthopedic, Inc., Warsaw, IN (US)

(72) Inventors: Roger E. Harrington, Collierville, TN (US); Jerbrena C. Jacobs, Hernando, MS (US); Damodaragounder Gopal, Highland Heights, OH (US); Ke-Qing Ling, Painesville, OH (US); Marco Burello, Cleveland, OH (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/474,325

(22) Filed: Mar. 30, 2017

(65) Prior Publication Data

US 2017/0204132 A1 Jul. 20, 2017

Related U.S. Application Data

(63) Continuation of application No. 14/962,651, filed on Dec. 8, 2015, now Pat. No. 9,611,288.

(60) Provisional application No. 62/089,600, filed on Dec. 9, 2014, provisional application No. 62/089,607, filed on Dec. 9, 2014.

(51) Int. Cl.
| | | |
|---|---|---|
| *C07J 7/00* | (2006.01) | |
| *C07J 9/00* | (2006.01) | |
| *C07J 17/00* | (2006.01) | |
| *C07J 51/00* | (2006.01) | |

(52) U.S. Cl.
CPC ............ *C07J 9/00* (2013.01); *C07J 7/002* (2013.01); *C07J 17/00* (2013.01); *C07J 51/00* (2013.01)

(58) Field of Classification Search
CPC ..... C07J 9/00; C07J 7/002; C07J 17/00; C07J 51/00; A61K 31/575
See application file for complete search history.

(56) References Cited

U.S. PATENT DOCUMENTS

| | | | |
|---|---|---|---|
| 3,088,951 A | 5/1963 | Oberster | .................... C07J 5/00 540/89 |
| 7,897,588 B2 | 3/2011 | Parhami | |
| 8,022,052 B2 | 9/2011 | Parhami et al. | |
| 8,268,008 B2 | 9/2012 | Betz et al. | |
| 8,475,824 B2 | 7/2013 | McKay | |
| 8,586,070 B2 | 11/2013 | Briest | |
| 8,642,065 B2 | 2/2014 | Hans Moore et al. | |
| 8,877,221 B2 | 11/2014 | McKay | |
| 8,900,617 B2 | 12/2014 | McKay | |
| 9,611,288 B2 * | 4/2017 | Harrington | ................ C07J 9/00 |
| 9,657,052 B2 * | 5/2017 | Harrington | ................ C07J 9/00 |
| 2003/0009235 A1 | 1/2003 | Manrique et al. | |
| 2006/0251735 A1 | 11/2006 | Parhami | |
| 2006/0270645 A1 | 11/2006 | Parhami | |
| 2009/0202660 A1 | 8/2009 | Parhami | |
| 2009/0220562 A1 | 9/2009 | Parhami | |
| 2010/0034781 A1 | 2/2010 | Parhami | |
| 2010/0112030 A1 | 5/2010 | Parhami | |
| 2010/0119492 A1 | 5/2010 | Hans et al. | |
| 2011/0008297 A1 | 1/2011 | Parhami et al. | |
| 2011/0104230 A1 | 5/2011 | Mousa et al. | |
| 2011/0276147 A1 | 11/2011 | Cook et al. | |
| 2012/0107401 A1 | 5/2012 | McKay | |
| 2012/0265167 A1 | 10/2012 | Simonson et al. | |
| 2013/0244942 A1 | 9/2013 | Benedict et al. | |
| 2014/0170202 A1 | 6/2014 | Peters et al. | |
| 2014/0248372 A1 | 9/2014 | Boden et al. | |
| 2014/0335147 A1 | 11/2014 | Alexakis | |
| 2015/0118277 A1 | 4/2015 | Parhami et al. | |
| 2016/0159850 A1 | 6/2016 | Parhami | |

FOREIGN PATENT DOCUMENTS

| | | | |
|---|---|---|---|
| WO | 2009073186 A1 | 6/2009 | |
| WO | 2012024581 A2 | 2/2012 | |
| WO | 2012024584 A2 | 2/2012 | |
| WO | 2013169399 A1 | 11/2013 | |
| WO | 2014093836 A1 | 6/2014 | |
| WO | 2014179756 A1 | 11/2014 | |
| WO | WO-2014179756 A1 * | 11/2014 | ........... A61K 31/575 |
| WO | 2015009991 A2 | 1/2015 | |
| WO | 2015014872 A1 | 2/2015 | |

OTHER PUBLICATIONS

Zaragoza Dorwald, Side Reactions in Organic Synthesis, 2005, WILEY-VCH Verlag GmbH & Co. KGaA, Weinheim, Preface. p. IX . (Year: 2005).*
Stappenbeck et al, Bioorganic Medicinal Chemistry Letters, Novel Oxysterols Activate the Hedgehog Pathway and Induce Osteogenesis, 2012, 22, pp. 5893-5897 with supplementary data. (Year: 2012).*
Nedclu et al, Nature Chemical Biology, Oxysterol binding to the extracellular domain of Smoothened in Hedgehog signaling, 2003, 9, pp. 557-564, with Supplementary data pp. i-28.
Hoyte et al, Journal of Biological Chemistry, Enzymatic Side Chain Cleavage of C-20 Alkyl and Aryl Analogs of (20-S)-20-Hydroxycholesterol, 1979, 254(7), pp. 2278-2286.
Zaragoza Dorwald, Side Reactions in Organic Synthesis, 2005, WILEY-VCH Verlag GmbH & Co. KGaA, Weinheim, Preface. p. IX.

(Continued)

*Primary Examiner* — Paul A Zucker

(57) ABSTRACT

Compounds and methods of synthesizing oxysterols are provided. The compounds and methods provided allow the oxysterol to be safely produced at a high yield. The compounds and methods provided can produce the oxysterol in a stereoselective manner. The method comprises reacting a diol with borane and hydrogen peroxide to form the oxysterol or a pharmaceutically acceptable salt, hydrate or solvate thereof.

7 Claims, 7 Drawing Sheets

(56) References Cited

OTHER PUBLICATIONS

Stappenbeck, Frank, et al. Novel oxysterols activate the Hedgehog pathway and induce osteogenesis. Bioorganic & Medicinal Chemistry Letters, vol. 22, p. 5893-5897, 2012 Elsevier Ltd.

International Search Report and Written Opinion for PCT/US2015/064526 the counterpart application dated Apr. 8, 2016.

Nedelcu et al. Oxysterol binding to the extracellular domain of Smoothened in Hedgehog signaling. Nature Chemical Biology 9(9): 557-564 (2013) Supplementary Information pp. 1-28, [retrieved on Mar. 9, 2016]. Retrieved from the Internet. <URL: http://www.nature.com/nchembio/journal/v9/n9/extref/nchembio.1290-S1.pdf> entire document.

Haren et al. Inhibition of cholesterol side-chain cleavage by intermediates of an alternative steroid biosynthetic pathway. FESS Letters 232(2): 377-380; 1988. [retrieved on Mar. 9, 2016]. Retrieved from the Internet. <URL:http://onlinelibrary.wiley.com/doi/10.1016/0014-5793(88) 80773-7/epdf>. entire document.

PubChem, Compound Summary for SID 113493311, Create Date: Mar. 11, 2011. [retrieved on Jan. 14, 2016]. Retrieved from the Internet. <URL: https://pubchem.ncbi.nlm.nih.gov/substance/113493311> entire document.

* cited by examiner

COMPOUNDS AND METHODS INVOLVING STEROLS

This application is a continuation of U.S. application Ser. No. 14/962,651 filed Dec. 8, 2015, entitled "COMPOUNDS AND METHODS INVOLVING STEROLS," now U.S. Pat. No. 9,611,288, which claims the benefit of the filing date of U.S. Provisional Application No. 62/089,607, filed Dec. 9, 2014, entitled "COMPOUNDS AND METHODS OF MAKING STEROLS USING DIOLS"; and U.S. Provisional Application No. 62/089,600, filed Dec. 9, 2014, entitled "COMPOUNDS AND METHODS INVOLVING STEROLS". These entire disclosures are hereby incorporated by reference into the present disclosure.

BACKGROUND

Biologics are commonly employed to promote bone growth in medical applications including fracture healing and surgical management of spinal disorders. Spine fusion is often performed by orthopedic surgeons and neurosurgeons alike to address degenerative disc disease and arthritis affecting the lumbar and cervical spine. Historically, autogenous bone grafting, commonly taken from the iliac crest of the patient, has been used to augment fusion between vertebral levels.

One protein that is osteogenic and commonly used to promote spine fusion is recombinant human bone morphogenetic protein-2 (rhBMP-2). Its use has been approved by the US Food and Drug Administration (FDA) for single-level anterior lumbar interbody fusion. The use of rhBMP-2 has increased significantly since this time and indications for its use have expanded to include posterior lumbar spinal fusion as well as cervical spine fusion.

Oxysterols form a large family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some naturally occurring oxysterols have robust osteogenic properties and can be used to grow bone. The most potent osteogenic naturally occurring oxysterol, 20(S)-hydroxycholesterol, is both osteogenic and anti-adipogenic when applied to multipotent mesenchymal cells capable of differentiating into osteoblasts and adipocytes.

One such oxysterol is Oxy133 or (3S,5S,6S,8R,9S,10R, 13S,14S,17S)17-4S)-2-hydroxyoctan-2-yl)-10,13-dimethyl-hexadecahydro-1H-cyclopenta[a]phenanthrene-3,6-diol, which exhibits the following structures:

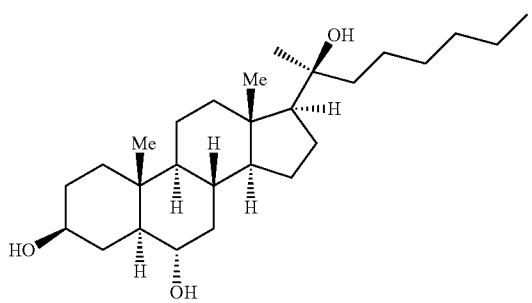

or

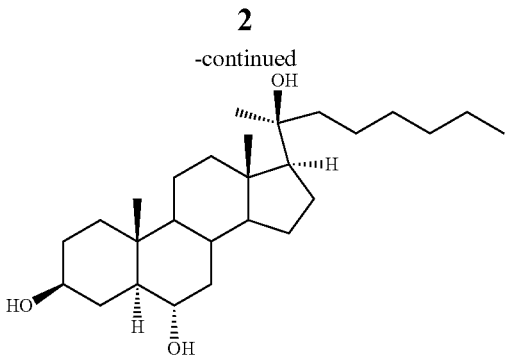

To synthesize Oxy133, often there are complex, multi-step chemical reactions that are difficult to carry out in a single container. For example, to synthesize Oxy133 there may be utilization of various protection reagents to protect end groups as the molecule is being synthesized. In addition, various deprotection reagents are also utilized that increase cost, reduce safety and have an adverse environmental impact. Further, the route of synthesis of OXY133 can have very low yield less than 30%.

Therefore, there is a need for a cost effective method of synthesizing Oxy133 for use in promoting osteogenesis, osteoinduction and/or osteoconduction. Methods of synthesizing Oxy133 having a high yield and improved process safety would be beneficial. Methods for synthesizing Oxy133 from endogenous starting material, which is stereoselective, would also be beneficial.

SUMMARY

Compounds and methods of synthesizing Oxy133 are provided for use in promoting osteogenesis, osteoinduction and/or osteoconduction Methods of synthesizing Oxy133 having high yields and improved process safety are also provided. Methods for synthesizing Oxy133 that are stereoselective are also provided. Methods of synthesizing Oxy133 that have reduced environmental impact and have low product cost are also provided.

In some embodiments, there is a compound comprising the structure:

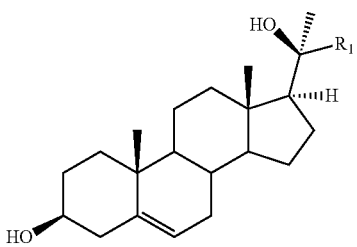

or a pharmaceutically acceptable salt, hydrate or solvate thereof, wherein R1 comprises an aliphatic or cyclic substituent having at least one carbon atom.

In some embodiments there is a method of making a sterol, the method comprising reacting a organometallic compound with pregnenolone or pregnenolone acetate to form the sterol, the sterol having the formula:

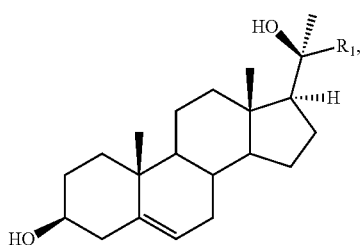

or a pharmaceutically acceptable salt, hydrate or solvate thereof, wherein R1 comprises an aliphatic or cyclic substituent having at least one carbon atom.

In some embodiments, there is a method of making an oxysterol, the method comprising reacting a diol having the formula:

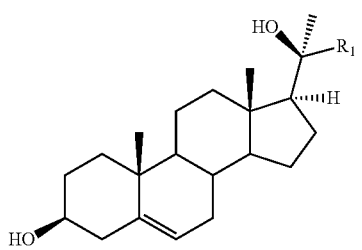

with borane and hydrogen peroxide to form the oxysterol or a pharmaceutically acceptable salt, hydrate or solvate thereof having the formula:

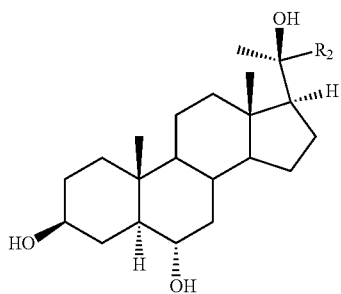

wherein R1 comprises an aliphatic or cyclic substituent having at least one carbon atom, and
wherein R2 comprises an aliphatic or cyclic substituent having at least one carbon atom.

In some embodiments, there is a method of making an oxysterol, the method comprising reacting a diol having the formula:

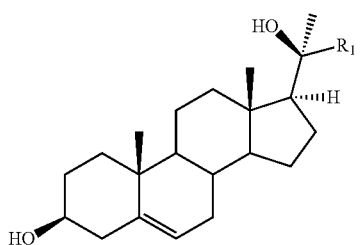

with a borane compound to form the oxysterol or a pharmaceutically acceptable salt, hydrate or solvate thereof having the formula:

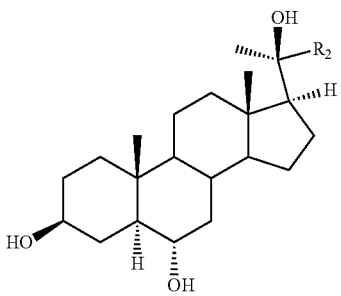

wherein R1 comprises an aliphatic or cyclic substituent having at least one carbon atom, and R2 comprises an aliphatic or cyclic substituent having at least one carbon atom.

In some embodiments, there is a method of making an oxysterol, the method comprising reacting a diol having the formula:

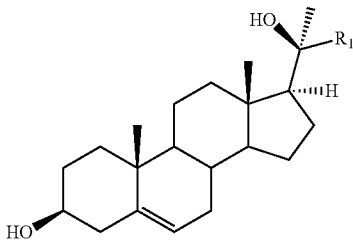

with borane, hydrogen peroxide and tetrahydrofuran to form the oxysterol or a pharmaceutically acceptable salt, hydrate or solvate thereof having the formula:

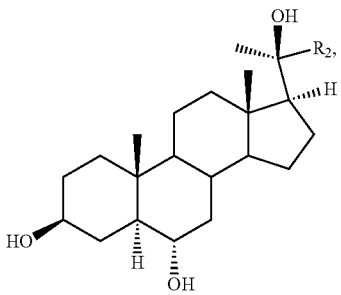

wherein R1 comprises an aliphatic or cyclic substituent having at least one carbon atom, and R2 comprises an aliphatic or cyclic substituent having at least one carbon atom.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
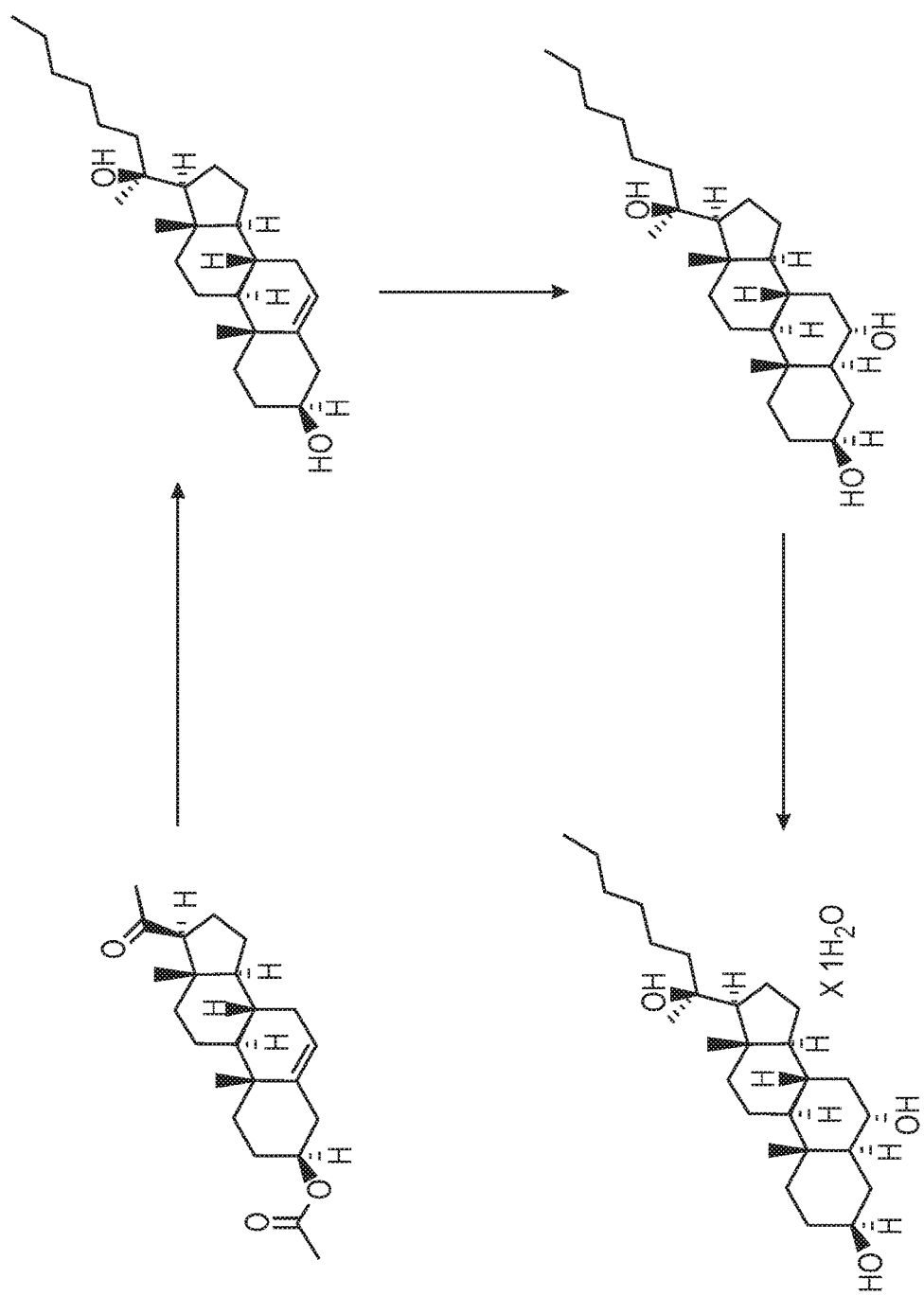
FIG. 1 illustrates a step-wise reaction for synthesizing Oxy133 with starting reactants comprising pregnenolone acetate, as shown in one embodiment of this disclosure. The pregnenolone is reacted with an organometallic compound to produce a sterol or diol having two hydroxyl groups. The sterol or diol is then reacted with borane and hydrogen peroxide and purified to produce Oxy133.
Figure 2:
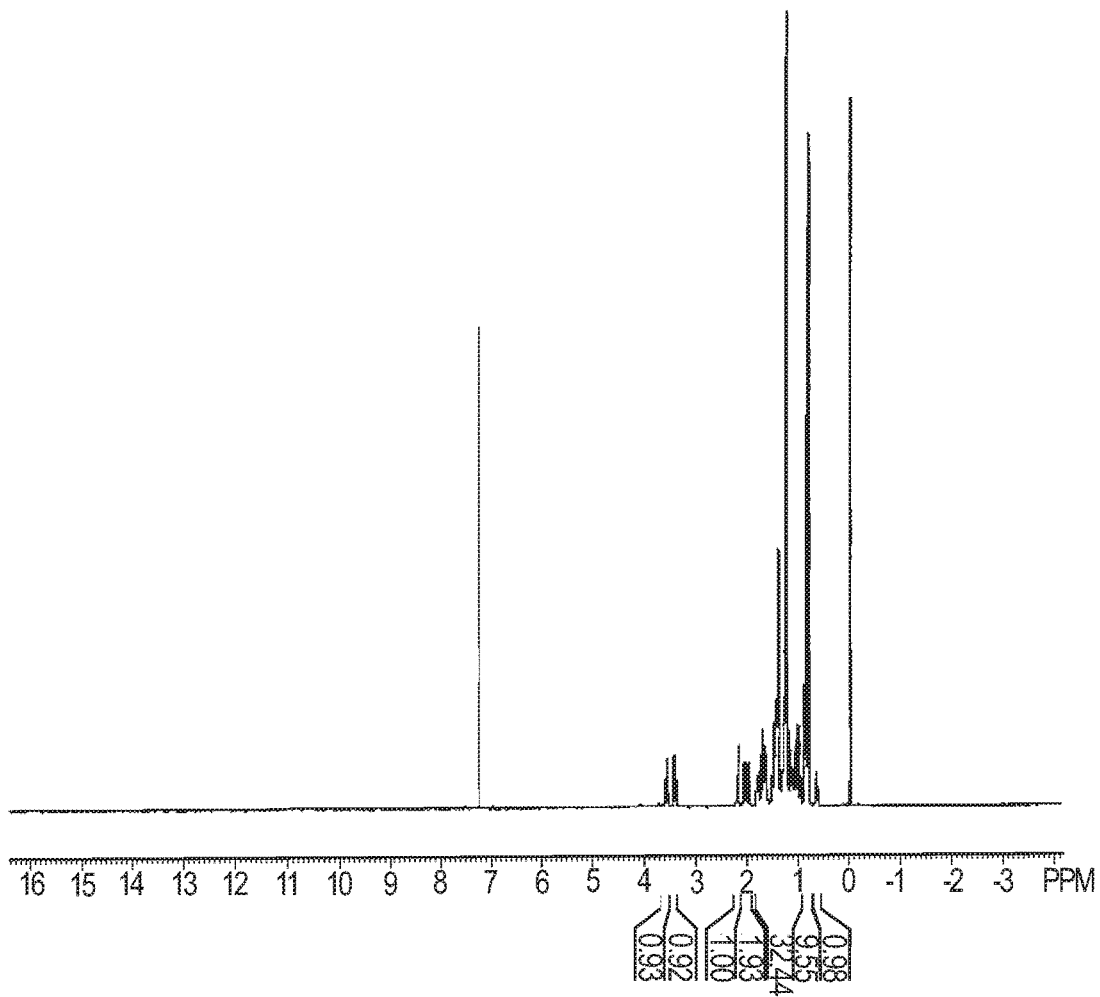
FIG. 2 is a graphic illustration of the $^1$H NMR data obtained from isolated and purified Oxy133.
Figure 3:
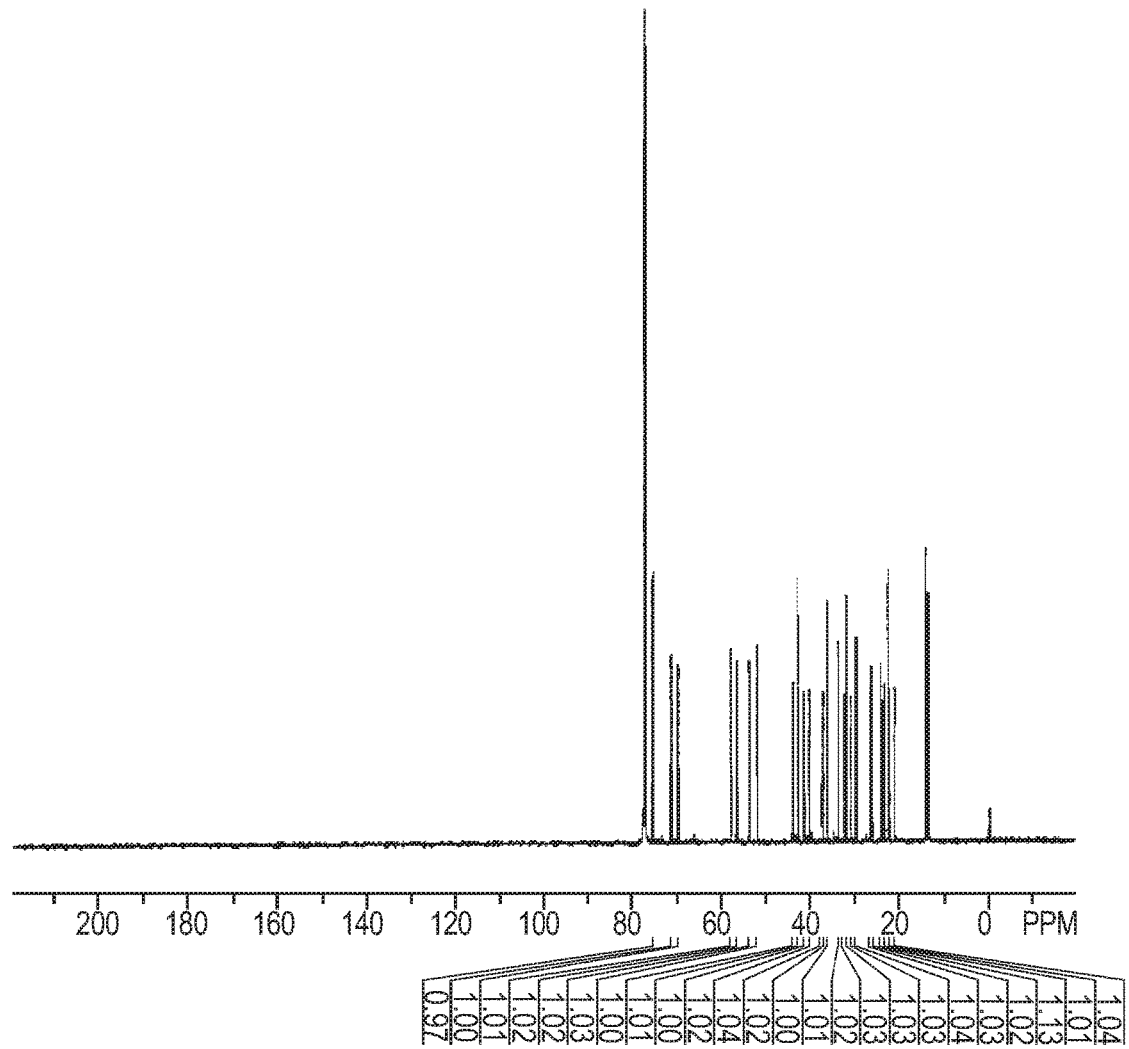
FIG. 3 is a graphic illustration of the $^{13}$C NMR data obtained from Oxy133.
Figure 4:
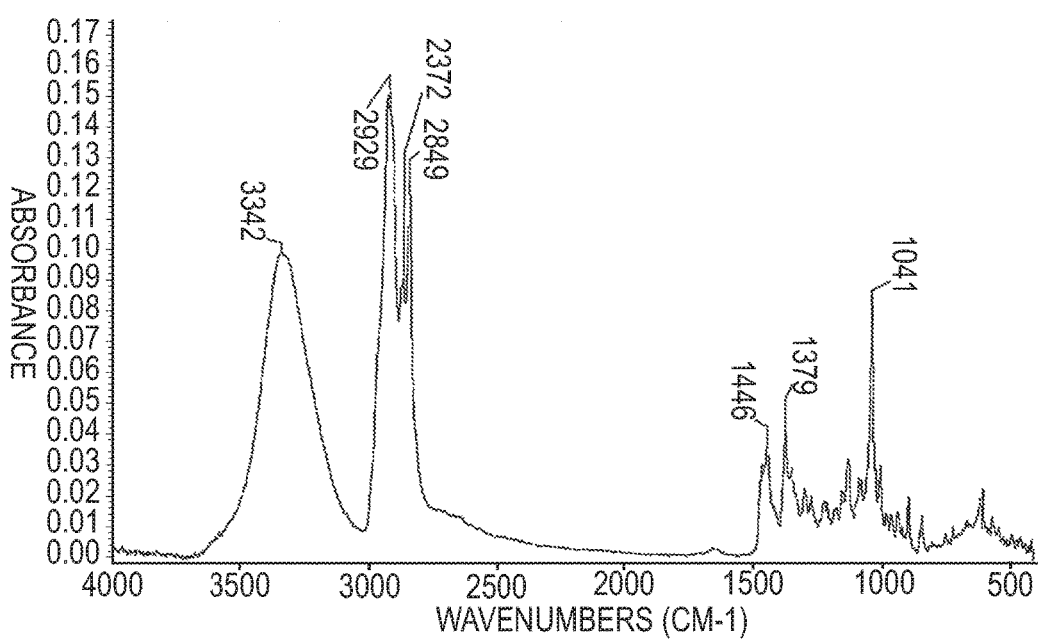
FIG. 4 is a graphic illustration of the infrared spectroscopy data obtained from Oxy133.
Figure 5:
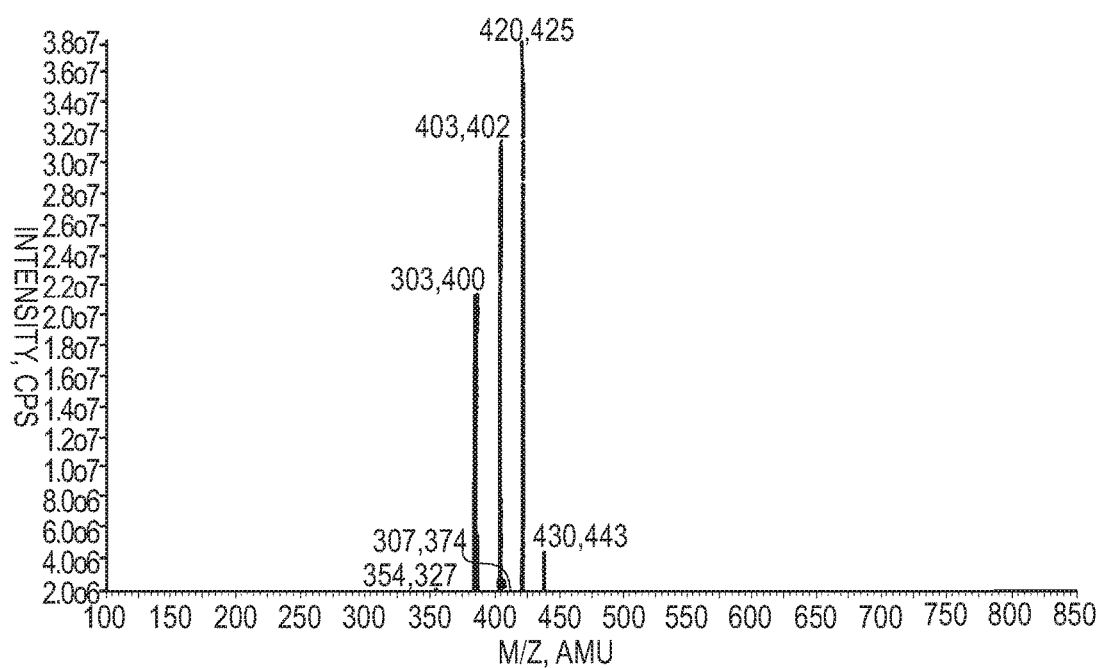
FIG. 5 is a graphic illustration of the mass spectroscopy data obtained from Oxy133.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an alkanolamine" includes one, two, three or more alkanolamines.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug".

The term "biodegradable" includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells) infiltrate the components and allow repair of the defect. By "bioerodible" it is meant that the compounds or components will erode or degrade over time due, at least in part, to contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The term "alkyl" as used herein, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl, propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl" and/or "alkynyl" is used, as defined below. In some embodiments, the alkyl groups are (C1-C40) alkyl. In some embodiments, the alkyl groups are (C1-C6) alkyl.

The term "alkanyl" as used herein refers to a saturated branched, straight-chain or cyclic alkyl radical derived by the removal of one hydrogen atom from a single carbon atom of a parent alkane. Typical alkanyl groups include, but are not limited to, methanyl; ethenyl; propanyls such as propan-1-yl, propan-2-yl(isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are (C1-C40) alkanyl. In some embodiments, the alkanyl groups are (C1-C6) alkanyl.

The term "alkenyl" as used herein refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1- yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is (C2-C40) alkenyl. In some embodiments, the alkenyl group is (C2-C6) alkenyl.

The term "alkynyl" as used herein refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In some embodiments, the alkenyl group is (C2-C40) alkynyl. In some embodiments, the alkynyl group is (C2-C6) alkynyl.

The term "alkyldiyl" as used herein refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl, cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is (C1-C40) alkyldiyl. In some embodiments, the alkyldiyl group is (C1-C6) alkyldiyl. Also contemplated are saturated acyclic alkanyldiyl radicals in which the radical centers are at the terminal carbons, e.g., methandiyl (methano); ethan-1,2-diyl(ethano); propan-1,3-diyl(propano); butan-1,4-diyl(butano); and the like (also referred to as alkylenos, defined infra).

The term "alkyleno" as used herein refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is (C1-C40) alkyleno. In some embodiments, the alkyleno group is (C1-C6) alkyleno.

The terms "heteroalkyl," "heteroalkanyl," "heteroalkenyl," "heteroalkanyl," "heteroalkyldiyl" and "heteroalkyleno" as used herein refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR', =N—N=, —N=N—, —N(O)N—, —N=N—NR'—, —PH—, —P(O)2-, —O—P(O)2-, —SH2-, —S(O)2-, or the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

The term "aryl" as used herein refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is (C5-C14) aryl or a (C5-C10) aryl. Some preferred aryls are phenyl and naphthyl.

The term "aryldiyl" as used herein refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryldiyl group is (C5-C14) aryldiyl or (C5-C10) aryldiyl. For example, some preferred aryldiyl groups are divalent radicals derived from benzene and naphthalene, especially phena-1,4-diyl, naphtha-2,6-diyl and naphtha-2,7-diyl.

The term "arydeno" as used herein refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

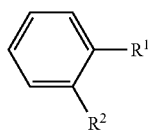

wherein $R^1$, when taken alone is hydrogen, or when taken together with $R^2$ is (C5-C14) aryleno; and $R^2$, when taken alone is hydrogen, or when taken together with $R^1$ is (C5-C14) aryleno.

When $R^1$ and $R^2$ are each hydrogen, the resultant compound is benzene. When $R^1$ taken together with $R^2$ is C6 aryleno (benzeno), the resultant compound is naphthalene. When $R^1$ taken together with $R^2$ is C10 aryleno (naphthaleno), the resultant compound is anthracene or phenanthrene. Typical aryleno groups include, but are not limited to, aceanthryleno, acenaphthyleno, acephenanthtyleno, anthraceno, azuleno, benzeno (benzo), chryseno, coroneno, fluorantheno, fluoreno, hexaceno, hexapheno, hexyleno, as-indaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2]benzo), [1,2]naphthaleno, [2,3]naphthaleno, etc. Thus, in the above example, when $R^1$ taken together with $R^2$ is [2,3]naphthaleno, the resultant compound is anthracene. When $R^1$ taken together with $R^2$ is [1,2]naphthaeno, the resultant compound is phenanthrene. In a preferred embodiment, the aryleno group is (C5-C14), with (C5-C10) being even more preferred.

The term "arylaryl" as used herein refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. When the number of carbon atoms comprising an arylaryl group is specified, the numbers refer to the carbon atoms comprising each parent aromatic ring. For example, (C1-C14) arylaryl is an arylaryl group in which each aromatic ring comprises from 5 to 14 carbons, e.g., biphenyl, triphenyl, binaphthyl, phenylnaphthyl, etc. In some instances, each parent aromatic ring system of an arylaryl group is independently a (C5-C14) aromatic or a (C1-C10) aromatic. Some preferred are arylaryl groups in which all of the parent aromatic ring systems are identical, e.g., biphenyl, triphenyl, binaphthyl, trinaphthyl, etc.

The term "biaryl" as used herein refers to an arylaryl radical having two identical parent aromatic systems joined directly together by a single bond. Typical biaryl groups include, but are not limited to, biphenyl, binaphthyl, bianthracyl, and the like. In some instances, the aromatic ring systems are (C5-C14) aromatic rings or (C5-C10) aromatic rings. One preferred biaryl group is biphenyl.

The term "arylalkyl" as used herein refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C6-C40) arylalkyl, e.g., the alkanyl, alkenyl or alkynyl moiety of the arylalkyl group is (C1-C26) and the aryl moiety is (C5-C14). In some preferred embodiments the arylalkyl group is (C6-C13), e.g., the alkanyl, alkenyl or alkynyl moiety of the arylalkyl group is (C1-C3) and the aryl moiety is (C5-C10).

The term "heteroaryl" as used herein refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindo line, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl, with 5-10 membered heteroaryl being particularly preferred. Some preferred heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryldiyl group is 5-14 membered heteroaryldiyl or a 5-10 membered heteroaryldiyl. Some preferred heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryleno" as used herein refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

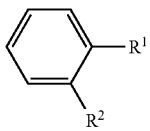

wherein $R^1$, when taken alone is hydrogen, or when taken together with $R^2$ is 5-14 membered heteroaryleno; and $R^2$, when taken alone is hydrogen, or when taken together with $R^1$ is 5-14 membered heteroaryleno;

When $R^1$ and $R^2$ are each hydrogen, the resultant compound is benzene. When R1 taken together with $R^2$ is a 6-membered heteroaryleno pyridino), the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, furan, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, or the like. Where a specific connectivity is intended, the involved bridging atoms (of the heteroaryleno bridge) are denoted in brackets, e.g., [1,2] pyridino, [2,3]pyridino, [3,4]pyridino, etc. Thus, in the above example, when $R^1$ taken together with $R^2$ is [1,2] pyridino, the resultant compound is quinolizine. When $R^1$ taken together with R2 is [2,3]pyridino, the resultant compound is quinoline. When $R^1$ taken together with $R^2$ is [3,4]pyridino, the resultant compound is isoquinoline. In preferred embodiments, the heteroaryleno group is 5-14 membered heteroaryleno or 5-10 membered heteroaryleno. Some preferred heteroaryleno radicals are those derived from parent heteroaromatic ring systems in which any ring heteroatoms are nitrogens, such as imidazolo, indole, indazolo, isoindolo, naphthyridino, pteridino, isoquinoline, phthalazino, purino, pyrazolo, pyrazino, pyridazino, pyndmo, pyrrolo, quinazolino, quinolino, etc.

The term "heteroaryl-heteroaryl" as used herein refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridyl-purinyl, bipurinyl, etc. When the number of ring atoms are specified, the numbers refer to the number of atoms comprising each parent heteroaromatic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. In some embodiments, each parent heteroaromatic ring system is independently a 5-14 membered heteroaromatic, more preferably a 5-10 membered heteroaromatic. Also preferred are heteroaryl-heteroaryl groups in which all of the parent heteroaromatic ring systems are identical. Some preferred heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "biheteroaryl" as used herein refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-14 membered heteroaromatic rings or 5-10 membered heteroaromatic rings. Some preferred biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

The term "heteroarylalkyl" as used herein refers to an acyclic alkyl radical in which one of the hydrogen atoms bonded to a carbon atom, typically a terminal or sp2 carbon atom, is replaced with a heteroaryl radical. Where specific alkyl moieties are intended, the nomenclature heteroarylalkanyl, heteroarylakenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In some preferred embodiments, the heteroarylalkyl is a 5-13 membered heteroarylalkyl, e.g., the alkanyl, alkenyl or alkynyl moiety is 1-3 membered and the heteroaryl moiety is a 5-10 membered heteroaryl.

The term "substituted" as used herein refers to a radical in which one or more hydrogen atoms are each independently replaced with the same or different substituent(s). Typical substituents include, but are not limited to, —X, —R, —O—, =O, —OR, —O—OR, —SR, —S—, =S, —NRR, =NR, perhalo (C1-C6) alkyl, —CX3, —CN, —OCN, —SCN, —NCO, —NCS, —NO, —NO2, =N2, —N3, —S(O)2O, —S(O)2OH, —S(O)2R, —C(O)R, —C(O)X, —C(S)R, —C(S)X, —C(O)OR, —C(O)O—, —C(S)OR, —C(O)SR, —C(S)SR, —C(O)NRR, —C(S)NRR and —C(NR)NRR, where each X is independently a halogen (e.g., —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

The term "solvate" as used herein refers to an aggregate that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be inorganic solvents such as for example water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol, sterol or diol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol, sterol or diol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol, sterol, or diol to assist in obtaining a controlled release depot effect, the oxysterol, sterol, or diol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The term "solvate" is a complex or aggregate formed by one or more molecules of a solute, e.g. a compound or a pharmaceutically-acceptable salt thereof and one or more molecules of a solvent. Such solvates can be crystalline solids having a substantially fixed molar ratio of solute and solvent. Suitable solvents include for example, water, ethanol, etc.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure. Sometimes the phrase "administration of Oxy133" is used herein in the context of administration of this compound to a subject (e.g., contacting the subject with the compound, injecting the compound, administering the compound in a drug depot, etc.). It is to be understood that the compound for such a use can generally be in the form of a pharmaceutical composition or bioactive composition comprising the Oxy133.

A "therapeutically effective amount" or "effective amount" is such that when administered, the oxysterol (e.g., Oxy133), sterol, diol, results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microliters particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a bone cavity, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, 99.9% or 99.999% less than the oral dosage or injectable dose.

The term "mammal" refers to organisms from the taxonomy class "mammalian," including but not limited to humans, other primates such as chimpanzees, apes, orangutans and monkeys, rats, mice, cats, dogs, cows, horses, etc.

The oxysterol can be "osteogenic," where it can enhance or accelerate the ingrowth of new bone tissue by one or more mechanisms such as osteogenesis, osteoconduction and/or osteoinduction.

New compositions and methods are provided to efficiently and safely make oxysterols including Oxy133. Methods and compositions that can efficiently and safely generate Oxy133 are also provided.

The section headings below should not be restricted and can be interchanged with other section headings.

Oxysterols

The present disclosure includes an osteogenic oxysterol (e.g., Oxy133), sterol, or diol and its ability to promote osteogenic differentiation in vitro. Oxy133 is a particularly effective osteogenic agent. In various applications, Oxy133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of Oxy133 is that it provides greater ease of synthesis and improved time to fusion when compared to other osteogenic oxysterols. Oxy133 is a small molecule that can serve as an anabolic therapeutic agent for bone growth, as well as a useful agent for treatment of a variety of other conditions.

One aspect of the application disclosure is a compound, named Oxy133, having the formula:

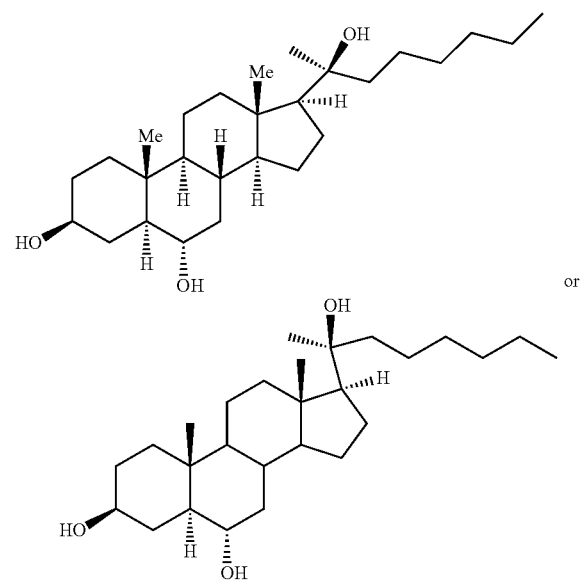

or a pharmaceutically acceptable salt, solvate or hydrate thereof. The Oxy133 may be used as a bioactive or pharmaceutical composition comprising Oxy133 or a pharmaceutically acceptable salt, solvate or hydrate thereof and a pharmaceutically acceptable carrier.

Another aspect of the disclosure is a method for inducing (stimulating, enhancing) a hedgehog (Hh) pathway mediated response, in a cell or tissue, comprising contacting the cell or tissue with a therapeutically effective amount of Oxy133. The cell or tissue can be in vitro or in a subject, such as a mammal. The hedgehog (Hh) pathway mediated response involves the stimulation of osteoblastic differentiation, osteomorphogenesis, and/or osteoproliferation; the stimulation of hair growth and/or cartilage formation; the stimulation of neovasculogenesis, e.g. angiogenesis, thereby enhancing blood supply to ischemic tissues; or it is the inhibition of adipocyte differentiation, adipocyte morphogenesis, and/or adipocyte proliferation; or the stimulation of progenitor cells to undergo neurogenesis. The Hh mediated response can comprise the regeneration of any of a variety of types of tissues, for use in regenerative medicine. Another aspect of the disclosure is a method for treating a subject having a bone disorder, osteopenia, osteoporosis, or a bone fracture, comprising administering to the subject an effective amount of a bioactive composition or pharmaceutical composition comprising Oxy133. The subject can be administered the bioactive composition or pharmaceutical composition at a therapeutically effective dose in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose in an effective dosage form at a selected interval to ameliorate the symptoms of osteoporosis. In some embodiments, a composition comprising Oxy133 may include mesenchymal stem cells to induce osteoblastic differentiation of the cells at a targeted surgical area.

In various aspects, the Oxy133 can be administered to a cell, tissue or organ by local administration. For example, the Oxy133 can be applied locally with a cream or the like, or it can be injected or otherwise introduced directly into a cell, tissue or organ, or it can be introduced with a suitable medical device, such as a drug depot as discussed herein.

In some embodiments, the dosage of Oxy133, sterol, or diol is from approximately 10 pg/day to approximately 80 mg/day. Additional dosages of Oxy133, sterol, or diol include from approximately 2.4 ng/day to approximately 50 mg/day; approximately 50 ng/day to approximately 2.5 mg/day; approximately 250 ng/day to approximately 250 mcg/day, approximately 250 ng/day to approximately 50 mcg/day; approximately 250 ng/days to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day.

In addition to the compound Oxy133, sterol, or diol other embodiments of the disclosure encompass any and all individual stereoisomers at any of the stereocenters present in Oxy133, including, diastereomers, racemates, enantiomers, and other isomers of the compound. In embodiments of the disclosure, Oxy133, sterol, oxysterol, diol may include all polymorphs, solvates or hydrates of the compound, such as hydrates and those formed with organic solvents.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts. Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate salicylate, stearate, sulfate, subacetate, succinate, tannate, tartrate, teoclate, tosylate, triethiodide and valerate salts of the compounds.

In various embodiments, Oxy133, sterol, or diol includes one or more biological functions. That is, Oxy133, sterol, or diol can induce a biological response when contacted with a mesenchymal stem cell or a bone marrow stromal cell. For example, Oxy133, sterol, or diol may stimulate osteoblastic differentiation. In some embodiments, a bioactive composition including Oxy133 sterol, or diol may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

Methods of Making Intermediary Diol

In some embodiments, the current disclosure provides a method for the preparation of an intermediary diol used in the production of Oxy133, as shown below. The diol may be used to promote bone growth as well. Previous methods of synthesis for Oxy133 produce were inefficient and not suitable for scale up manufacturing. Some stereoisomers of Oxy133 perform less optimally than others. The disclosed method is stereoselective and produces a high yield of the specific isomeric form of the diol shown below, which has been shown to produce an optimally effective isomeric form of Oxy133.

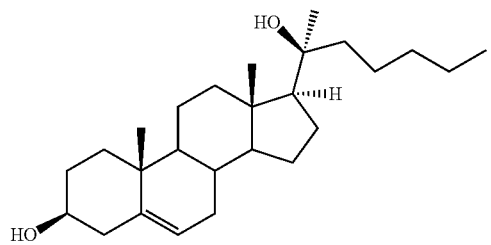 [SMILES: CCCCC[C@](C)(O)[C@H]1CCC2C3CC=C4C[C@@H](O)CC[C@]4(C)C3CC[C@@]21C]

Disclosed are multiple embodiments of reactions to synthesize the intermediary diol. The diol synthesized has the IUPAC designation (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Generally, the method of synthesizing the diol includes reacting pregnenolone, pregnenolone acetate or a pregnenolone derivative with an organometallic reagent to facilitate alkylation of the C17 position, as shown below:

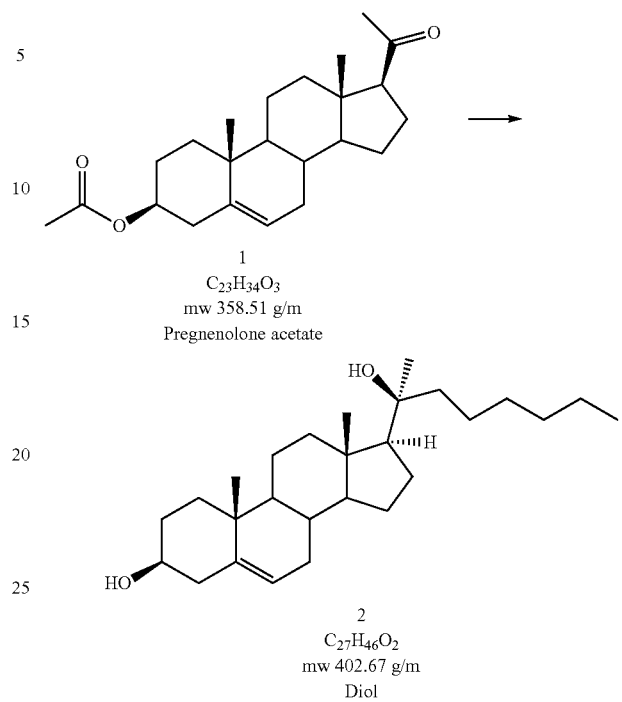

Scheme 1

1
$C_{23}H_{34}O_3$
mw 358.51 g/m
Pregnenolone acetate

2
$C_{27}H_{46}O_2$
mw 402.67 g/m
Diol

In one embodiment, as shown above in scheme 1, pregnenolone acetate (formula 1) may be alkylated by an organometallic reagent to synthesize the intermediary diol, shown above as formula 2. In some embodiments, pregnenolone acetate is reacted with a Grignard reagent to facilitate alkylation of the C17 position on the pregnenolone acetate molecule. In some embodiments, n-hexylmagnesium chloride is used as the organometallic reagent.

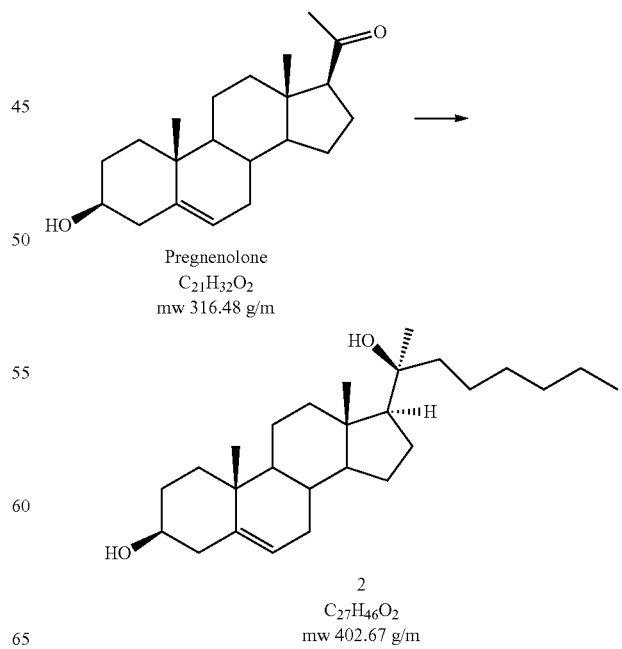

Scheme 2

Pregnenolone
$C_{21}H_{32}O_2$
mw 316.48 g/m

2
$C_{27}H_{46}O_2$
mw 402.67 g/m

In some embodiments, as shown above as scheme 2, pregnenolone is reacted with a Grignard reagent such as n-hexylmagnesium chloride to facilitate alkylation of the C17 position of the pregnenolone molecule to form the intermediary diol shown as formula 2.

The method of synthesizing the intermediary diol (formula 2) or (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol is stereoselective and produces a high yield of the diol. For example, in some embodiments, the yield of the desired stereoisomer of the diol is between about 60% and about 70%. In some embodiments, the yield of the desired stereoisomer of the diol is between about 50% and about 60%. However, it is contemplated that the percent yield may be higher or lower than these amounts. For example, the percent yield of formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the alkylation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, pregnenolone or pregnenolone acetate is used as a starting reactant. However, in other embodiments, derivatives of pregnenolone acetate may be used. For example, other specific examples of compounds which could be used in the present disclosure include: pregnenolone sulfate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3β-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, 21-thiol esters of pregnenolone sulfate, pyridinium, imidazolium, 6-methylpregnenolone sulfate, 6,16α-dimethylpregnenolone sulfate, 3β-hydroxy-6-methylpregna-5,16-dien-20-one sulfate, 3β-hydroxy-6,16-dimethylpregna-5,16-dien-20-one sulfate, 3jβ-hydroxypregna-5,16-dien-20-one sulfate, diosgenin sulfate, 3β-hydroxyandrost-5-en-17β-carboxylic acid methyl ester sulfate, 3α hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol-3-methyl ether, 17-deoxyestrone, and 17β-hydroxyestra-1,3,5(10)-trien-3-yl carboxymethyl ether.

In some embodiments, the organometallic comprises n-hexylmagnesium chloride. However, in some embodiments, the alkylation reaction may be carried out with the use of an alkyllithium, such as, for example, n-hexyllithium.

In various embodiments, the organometallic includes an alkyl halide. For example, the organometallic reagent may have the following formula:

where Mg comprises magnesium, X comprises chlorine, bromine, fluorine, iodine, or astatine and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a (C1-C20) alkyl or heteroalkyl, a (C2-C20) aryl or heteroaryl, a (C6-C26) arylalkyl or heteroalkyl and a (C5-C20) arylalkyl or heteroaryl-heteroalkyl, a $(C_4-C_{10})$ alkyldiyl or heteroalkyldiyl, or a $(C_4-C_{10})$ alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group in some embodiments, the R substituent is a hexyl group.

Alternatively, the organometallic may comprise the formula:

where Li comprises lithium and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, as arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a $(C_1-C_{20})$ alkyl or heteroalkyl, a $(C_2-C_{20})$ aryl or heteroaryl, a $(C_6-C_{26})$ arylalkyl or heteroalkyl and a $(C_5-C_{20})$ arylalkyl or heteroaryl-heteroalkyl, a $(C_4-C_{10})$ alkyldiyl or heteroalkyldiyl, or a $(C_4-C_{10})$ alkyleno or heteroalkyleno. The substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

In some embodiments, the alkylation reaction is exothermic and the reaction vessel may be temperature controlled to maintain optimal reaction kinetics. In some embodiments, the exothermic reaction releases about 1000 BTU per pound of solution. Due to the strongly exothermic nature of the reaction, the Grignard reagent therefore must be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 15° C., 10° C., 5° C. or 1° C. In some embodiments, the reaction vessel is maintained at about 0° C. during the alkylation reaction to form the intermediary diol of formula 2.

In various embodiments, the diol of formula 2 is synthesized along with byproducts and can be purified. For example, the resulting diol of formula 2 may be a byproduct of a diastereomeric mixture. In various embodiments, the diol of formula 2 may be isolated and purified. That is, the diol of formula 2 can be isolated and purified to the desired purity, e.g., from about 95% to about 99.9% by filtration, centrifugation, distillation, which separates volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. The diol may be purified by contacting it with organic and/or inorganic solvents, for example, THF, water, diethyl ether, dichloromethane, ethyl acetate, acetone, n,n-dimethylformamide, acetonitrile, dimethyl sulfoxide, ammonia, t-butanol, n-propanol, ethanol, methanol, acetic acid, or a combination thereof.

In various embodiments, the alkylation step and the purification step take place in the same reaction vessel.

In some embodiments, the diol is quenched with aqueous ammonium chloride or acetic acid to reduce the amount of anions present and neutralize the reaction and separated from the resulting organic layer. The separated residue is recovered by evaporation and purified by silica gel column chromatography.

The diol may be anhydrous or in the monohydrate form. However, in other embodiments the purified diol may be crystallized in other hydrous forms, such as, for example, a dihydrate, a hemihydrate, a sesquihydrate, a trihydrate, a tetrahydrate and the like, as well as the corresponding solvated forms. In other embodiments, the purified diol is crystallized as a co-crystal or a pharmaceutically acceptable salt.

Methods of Making Oxy133

In some embodiments, the current disclosure provides a method for the preparation of an Oxy133, as shown below. Previous methods of synthesis for Oxy133 produce diastereomeric mixtures of Oxy133 intermediates which require purification methods to separate. As discussed above to form the intermediary diol, the disclosed method is stereoselective and produces a high yield of the specific isomeric forms of Oxy133. The formula of Oxy133 is shown below.

Disclosed are multiple embodiments of reactions to synthesize Oxy133. Oxy133 has the IUPAC designation (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol. Oxy133 has previously been synthesized through a complex process not suitable for scale-up as shown below:

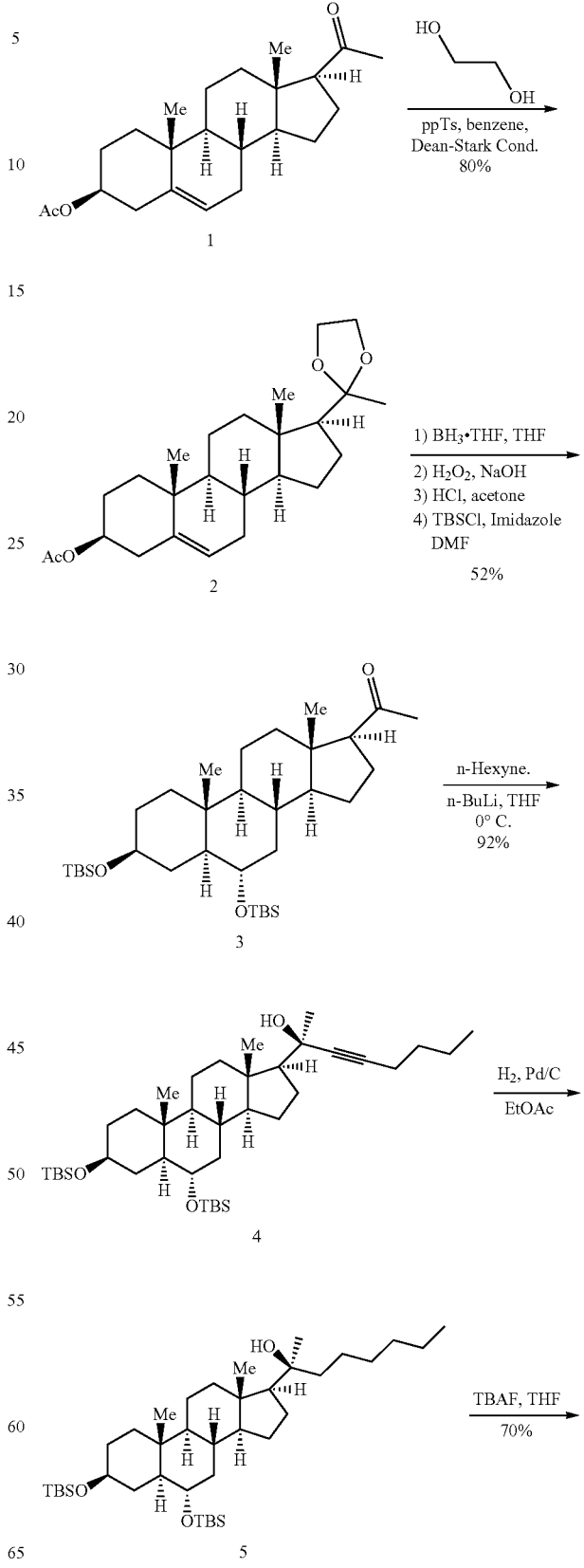

Scheme 3

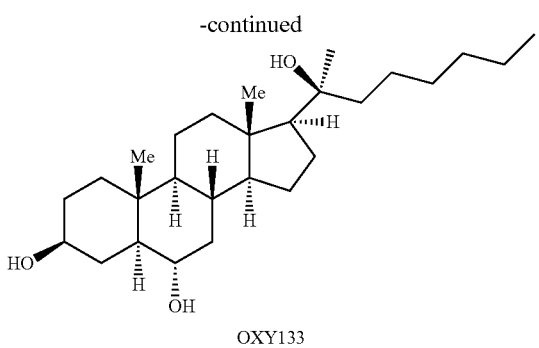

OXY133

However, the reaction has difficulty being carried out in a single container. The reaction shown above involves more reagents to carry out reaction steps (e.g., blocking and deprotection groups and steps) which have an adverse environmental impact. Additionally, the known methods involve reagents that are expensive and often difficult to obtain. Further, the method shown in Scheme 3 gives relatively low yields, has more degradation products, impurities and creates many toxic byproducts.

Generally, the method of synthesizing Oxy133 as disclosed herein includes reacting the diol synthesized as described herein with borane in the reaction shown below:

Scheme 4

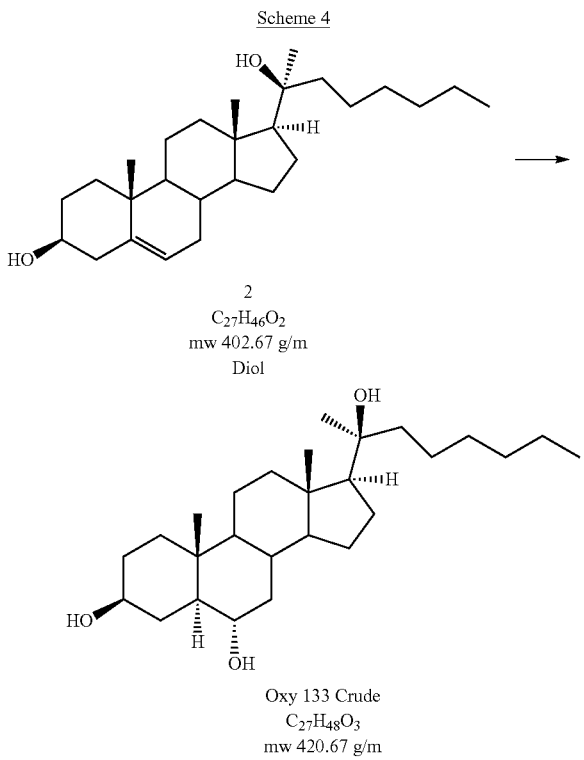

2
$C_{27}H_{46}O_2$
mw 402.67 g/m
Diol

Oxy 133 Crude
$C_{27}H_{48}O_3$
mw 420.67 g/m

In some embodiments, crude and unpurified Oxy133 is produced through a hydroboration and oxidation reaction of the intermediary diol having formula 2 in reaction scheme 4. Borane compounds that can be used in the reaction include $BH_3$, $B_2H_6$. $BH_3S(CH_3)_2$ (BMS), borane adducts with phosphines and amines, e.g., borane triethylamine; monosubstituted boranes of the form $RBH_2$ where R=alkyl and halide, monoalkyl boranes (e.g., $IpcBH_2$, monoisopinocampheylborane), monobromo- and monochloro-borane, complexes of monochloroborane and 1,4-dioxane, disubstituted boranes including bulky boranes, such as for example, dialkylborane compounds such as diethylborane, bis-3-methyl-2-butylborane (disiamylborane), 9-borabycyclo[3,3,1]nonane (9-BBN), disiamylborane (Sia2BH), dicyclohexylborane, Chx2BH, trialkylboranes, dialkylhalogenoboranes, dimesitylborane $(C_6H_2Me_3)_2BH$, alkenylboranes, pinacolborane, or catecholborane or a combination thereof.

Briefly, a hydroboration and oxidation reaction is a two-step reaction. The boron and hydrogen add across the double bond of an alkene to form a complex with the alkene. Thus the boration phase of the reaction is stereoselective and regioselective. The oxidation phase of the reaction involves basic aqueous hydrogen peroxide to furnish a hydroxyl substituent in place of the boron. See Vollhart, K P, Schore, N E, 2007, Organic Chemistry: Structure and Function, Fifth Ed., New York, N.Y., Custom Publishing Company. Thus, the intermediary diol having formula 2 is reacted with borane and hydrogen peroxide to form crude Oxy133. In some embodiments, the step of forming crude Oxy133 takes place in the same reaction vessel as the alkylation reaction. In other embodiments, the step of forming crude Oxy133 takes place in a different reaction vessel as the alkylation reaction.

The hydroboration-oxidation step of the synthesis of Oxy133, like the step of forming the intermediary diol, is stereoselective and produces a high yield. For example, in some embodiments, the percent yield of crude Oxy133 may be higher or lower than these amounts. For example, the percent yield of formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the hydroboration-oxidation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, the hydroboration-oxidation reaction is exothermic and the reaction vessel must be temperature controlled to maintain optimal reaction kinetics. Specifically, the oxidation phase is extremely exothermic. Due to the strongly exothermic nature of the reaction, the hydrogen peroxide therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 10° C., 5° C., 1° C. or 0° C. In some embodiments, the reaction vessel is maintained at about −5° C. during the hydroboration-oxidation reaction.

In certain embodiments the diol can have a percent crystallinity of a salt, hydrate, solvate or crystalline form of diol to be at least 10%, at least 20%, at least 30%, at least 40%, at least 50%, at least 60%, at least 70%, at least 80%, at least 90%, at least 95%, or at least 99%. In some embodiments, the percent crystallinity can be substantially 100%, where substantially 100% indicates that the entire amount of diol appears to be crystalline as best can be determined using methods known in the art. Accordingly, therapeutically effective amounts of diol can include amounts that vary in crystallinity. These include instances where an amount of the crystallized diol in a solid form is subsequently dissolved, partially dissolved, or suspended or dispersed in a liquid.

Purification of Oxy133

In some embodiments, the crude Oxy133 must be separated from the reaction mixture prior to purification. In some embodiments, an organic solvent such as dichloromethane is added to the crude Oxy133 reaction mixture and the resulting organic layer is separated. Once separated, the crude Oxy133 exists as a semi-solid viscous mass. The crude Oxy133 may be dissolved by any suitable means (e.g., dichloromethane, etc.) and placed into a silica gel column with an organic solvent, such as methanol-ethyl acetate, to solvate the crude Oxy133. In some embodiments, the crude Oxy133 may be crystallized or recrystallized. In some embodiments, purified Oxy133 is formed by recrystallizing the crude Oxy133 in a 3:1 mixture of acetone/water, as shown below:

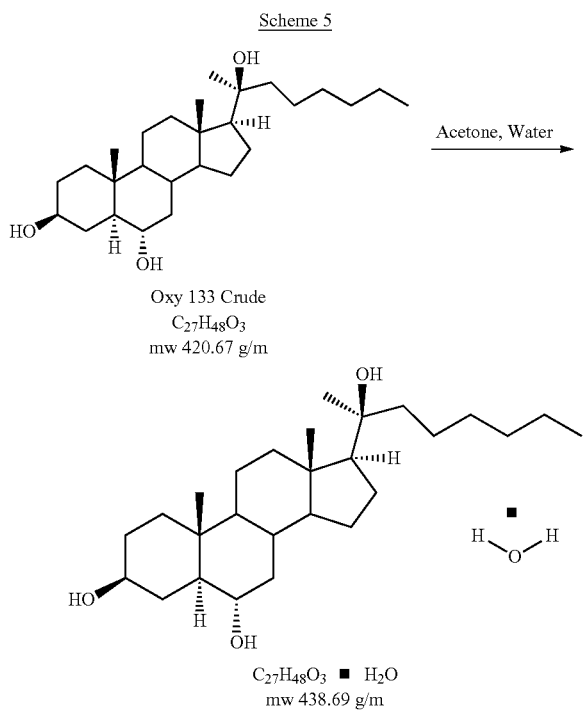

Scheme 5

As shown above, upon crystallization, the purified Oxy133 forms a hydrate. However, it can be in the anhydrous form. In some embodiments, the percent crystallinity of any of the crystalline forms of Oxy133 described herein can vary with respect to the total amount of Oxy133.

In certain embodiments the Oxy 133 can have a percent crystallinity of a salt, hydrate, solvate or crystalline form of Oxy133 to be at least 10%, at least 20%, at least 30%, at least 40%, at least 50%, at least 60%, at least 70%, at least 80%, at least 90%, at least 95%, or at least 99%. In some embodiments, the percent crystallinity can be substantially 100%, where substantially 100% indicates that the entire amount of Oxy133 appears to be crystalline as best can be determined using methods known in the art. Accordingly, therapeutically effective amounts of Oxy133 can include amounts that vary in crystallinity. These include instances where an amount of the crystallized Oxy133 in a solid form is subsequently dissolved, partially dissolved, or suspended or dispersed in a liquid.

In one embodiment, the purified Oxy133 is crystallized as a monohydrate. However, in other embodiments the purified Oxy133 may be crystallized in other hydrous forms, such as, for example, a dihydrate, a hemihydrate, a sesquihydrate, a trihydrate, a tetrahydrate and the like, as well as the corresponding solvated forms. In other embodiments, the purified Oxy133 is crystallized as a co-crystal or a pharmaceutically acceptable salt.

In some embodiments, the reaction mixture containing the crude Oxy133 may be solidified by mixing with heptanes. The product may subsequently be filtered and suspended in methylene chloride. In some embodiments, the crude Oxy133 may be filtered from the suspension and crystallized with the use of acetone and water or other organic or inorganic solvents (e.g., diethyl ether, dichloromethane, ethyl acetate, acetone, n,n-dimethylformamide, acetonitrile, dimethyl sulfoxide, ammonia, t-butanol, n-propanol, ethanol, methanol, acetic acid or a combination thereof).

In various embodiments, the crude Oxy133 may be isolated and purified by any other traditional means. That is, the crude Oxy133 can be isolated and purified to the desired purity, e.g., from about 95% to about 99.9% by filtration, centrifugation, distillation to separate volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. In various embodiments, the hydroboration-oxidation step and the purification step take place in the same reaction vessel. In various embodiments, the alkylation step, the hydroboration-oxidation step and the purification step take place in the same reaction vessel.

The method of synthesizing the intermediary diol (formula 2) is stereoselective and produces a high yield of Oxy133. For example, in some embodiments, the yield of the purified Oxy133 is between about 20% and about 99%. In some embodiments, the yield of the purified Oxy133 is between about 20% and about 80%. In some embodiments, the yield of the purified Oxy133 is between about 25% and about 70% or about 28%. However, it is contemplated that the percent yield may be higher or lower than these amounts.

In some embodiments, the purified Oxy133 is formed in crystal form via crystallization, which separates the Oxy133 from the liquid feed stream by cooling the liquid feed stream or adding precipitants which lower the solubility of byproducts and unused reactants in the reaction mixture so that the Oxy133 forms crystals. In some embodiments, the solid crystals are then separated from the remaining liquor by filtration or centrifugation. The crystals can be resolubilized in a solvent and then recrystallized and the crystals are then separated from the remaining liquor by filtration or centrifugation to obtain a highly pure sample of Oxy133. In some embodiments, the crystals can then be granulated to the desired particle size.

In some embodiments, the purity of the Oxy133 obtained is verified through nuclear magnetic resonance or mass spectroscopy. As shown in FIGS. 2-5, 1H NMR, 13C NMR, infrared spectroscopy, and mass spectroscopy analysis indicated that the Oxy133 product had high purity (e.g., having 98% to about 99.99% by weight purity).

In some embodiments, the crude Oxy133 can be purified where the purified Oxy133 is formed in crystalized form in a solvent and then removed from the solvent to form a high purity Oxy133 having a purity of from about 98% to about 99.99%. In some embodiments, the Oxy133 can be recovered via filtration or vacuum filtration before or after purification.

Use of Oxysterols

In use, Oxy133 provides therapeutic treatment for bone conditions. Oxy133 facilitates bone formation, osteoblastic differentiation, osteomorphogenesis and/or osteoproliferation. Treatment can be administered to treat open fractures and fractures at high risk of non-union, and in subjects with spinal disorders. That is, Oxy133 can induce spinal fusion and may help treat degenerative disc disease or arthritis affecting the lumbar or cervical vertebrae.

Mesenchymal stem cells treated with Oxy133 have been shown to have increased osteoblast differentiation. Thus, in some embodiments, Oxy133 may be implanted into a spinal site with mesenchymal stem cells to induce bone growth through osteoblast differentiation. Periosteum tissue is one tissue type that is involved early during normal bone fracture repair process and can recruit various cell types (e.g., mesenchymal stem cells) and bone growth factors necessary for bone fracture repair. Thus, in some embodiments, periosteum tissue is utilized as a source of mesenchymal stem cells and/or growth factors in a demineralized bone composition.

In some embodiments, the Oxy133 may be implanted or injected directly to a surgical site on a patient. In some embodiments, the Oxy133 obtained from the methods delineated above is in the form of a depot. In various embodiments, a plurality of depots (e.g., pellets) can be administered to a surgical site. In some embodiments, a plurality of depots are provided (e.g., in a kit) and administered to a surgical site and triangulate and/or surround the site needed for bone growth. In various embodiments, a plurality of depots comprise about 1, 2, 3, 4, 5, 6, 7, 8, 9 or 10 depots. In some embodiments, a plasticizer is used to lower glass translation temperature in order to affect stability of the device.

In various embodiments, the depot comprises Oxy133, sterol, or diol and a biodegradable polymer in amorphous, crystalline or semicrystalline form; where the crystalline form may include polymorphs, solvates or hydrates.

In some embodiments, Oxy133, sterol, or diol is administered in a device that is solid or in semi-solid form. The solid or semi-solid form of the device may have a pre-dosed viscosity in the range of about 1 to about 2000 centipoise (cps), 1 to about 200 cps, or 1 to about 100 cps. After the solid or semi-solid device is administered to the target site, the viscosity of the semi-solid or solid depot will increase and the semi-solid will have a modulus of elasticity in the range of about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In various embodiments, the semi-solid or solid depot may comprise a polymer having a molecular weight (MW), as shown by the inherent viscosity, from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 about 1.1 to about 1.3 dL/g, about 1.2 to about 1.4 dL/g, about 1.3 to about 1.5 about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the depot may not be fully biodegradable. For example, the device may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof. Typically, these types of matrices may need to be removed after a certain amount of time.

In various embodiments, the depot (e.g., device) may comprise a bioerodible, bioabsorbable, and/or a biodegradable biopolymer that may provide immediate release, or sustained release of the Oxy133. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), poly(esteramide)s, polyaspirins, polyphosphagenes, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide-caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In some embodiments, the depot comprises biodegradable polymers comprising wherein the at least one biodegradable polymer comprises one or more of poly(lactide-co-glycolide) (PLGA), polylactide polyglycolide (PGA), D-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof.

In some embodiments, the depot comprises at least one biodegradable material in a of about 99.5%, 99%, 98%, 97%, 96%, 95%, 94%, 93%, 92%, 91%, 90% 89%, 88%, 87%, 86%, 85%, 84%, 83%, 87%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

Mannitol, trehalose, dextran, mPEG and/or PEG may be used as a plasticizer for the polymer. In some embodiments, the polymer and/or plasticizer may also be coated on the depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the Oxy133, sterol, or diol from the depot (e.g., device). In some embodiments, the range of the coating on the depot ranges from about 5 microns to about 250 microns or 5 microns to about 200 microns to delay release from the device.

The depot (e.g., device) can be different sizes, shapes and configurations. There are several factors that can be taken into consideration in determining the size, shape and configuration of the depot. For example, both the size and shape may allow for ease in positioning the depot at the target tissue site that is selected as the implantation. In addition, the shape and size of the system should be selected so as to minimize or prevent the depot from moving after implantation. In various embodiments, the depot can be shaped like a rod or a flat surface such as a film or sheet (e.g., ribbon-like) or the like. Flexibility may be a consideration so as to facilitate placement of the device.

Radiographic markers can be included on the device to permit the user to position the depot (e.g., device) accurately into the target site of the patient. These radiographic markers will also permit the user to track movement and degradation of the depot (e.g., device) at the site over time. In this embodiment, the user may accurately position the depot (e.g., device) in the site using any of the numerous diagnostic imaging procedures. Such diagnostic imaging procedures include, for example, X-ray imaging or fluoroscopy. Examples of such radiographic markers include, but are not limited to, barium, phosphate, bismuth, iodine, tantalum, tungsten, and/or metal beads or particles. In various embodiments, the radiographic marker could be a spherical shape or a ring around the depot (e.g., device).

In some embodiments, the Oxy133, sterol, or diol can be administered to the target site using a "cannula" or "needle" that can be a part of a delivery device e.g., a syringe, a gun delivery device, or any medical device suitable for the application of Oxy133, sterol, or diol to a targeted organ or anatomic region. The cannula or needle of the device is designed to cause minimal physical and psychological trauma to the patient.

In some embodiments, the depot can be sutured to a target tissue site using a suturing needle. The dimensions of the needle, among other things, will depend on the site for implantation. For example, the width of the muscle planes in different surgical procedures can vary from 1-40 cm. Thus, the needle, in various embodiments, can be designed for these specific areas.

These and other aspects of the present application will be further appreciated upon consideration of the following Examples, which are intended to illustrate certain particular embodiments of the application but are not intended to limit its scope, as defined by the claims.

EXAMPLES

Example 1

Preparation from Pregnenolone Acetate 8.25 mL, n-hexylmagnesium chloride (2 M, 16.5 mmol) in THF was added to a solution of pregnenolone acetate in THF under vigorous electromagnetic stirring and ice bath cooling. The pregnenolone acetate solution contained 1.79 g compound 1, pregnenolone acetate, (5 mmol) in 4.5 mL THF. The addition took place over 2 minutes. After addition was completed, the mixture was stirred at room temperature for 3.5 hours, at which point the mixture had turned to a gel. The gel was then digested with a mixture of saturated aqueous NH$_4$Cl and MTBE (methyl tertiary-butyl ether). The organic layer was separated, washed with water three times and evaporated. The residue was separated by silica gel column chromatography using an EtOAc (ethyl acetate)/petroleum ether mixture (ratio 70/30) to give compound 2, a diol, as a white solid. 1.29 g (3.21 mmol) of the solid diol was extracted for a 64% isolated yield. The reaction is shown below in A:

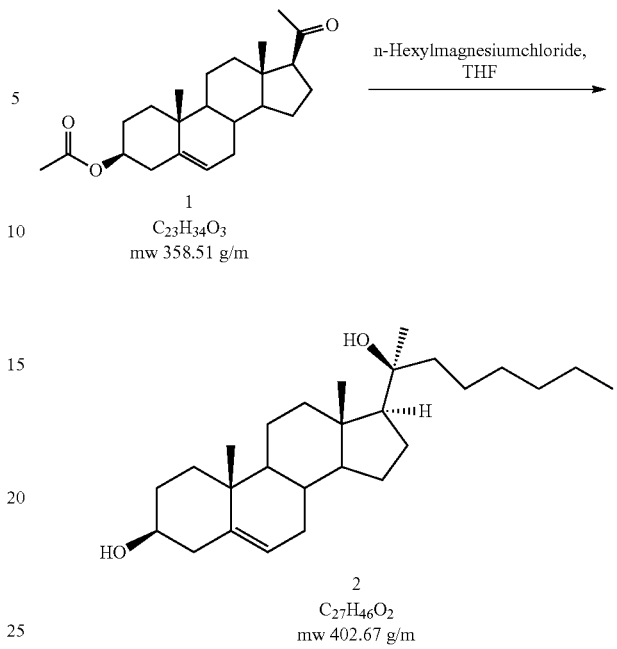

Figure 6:
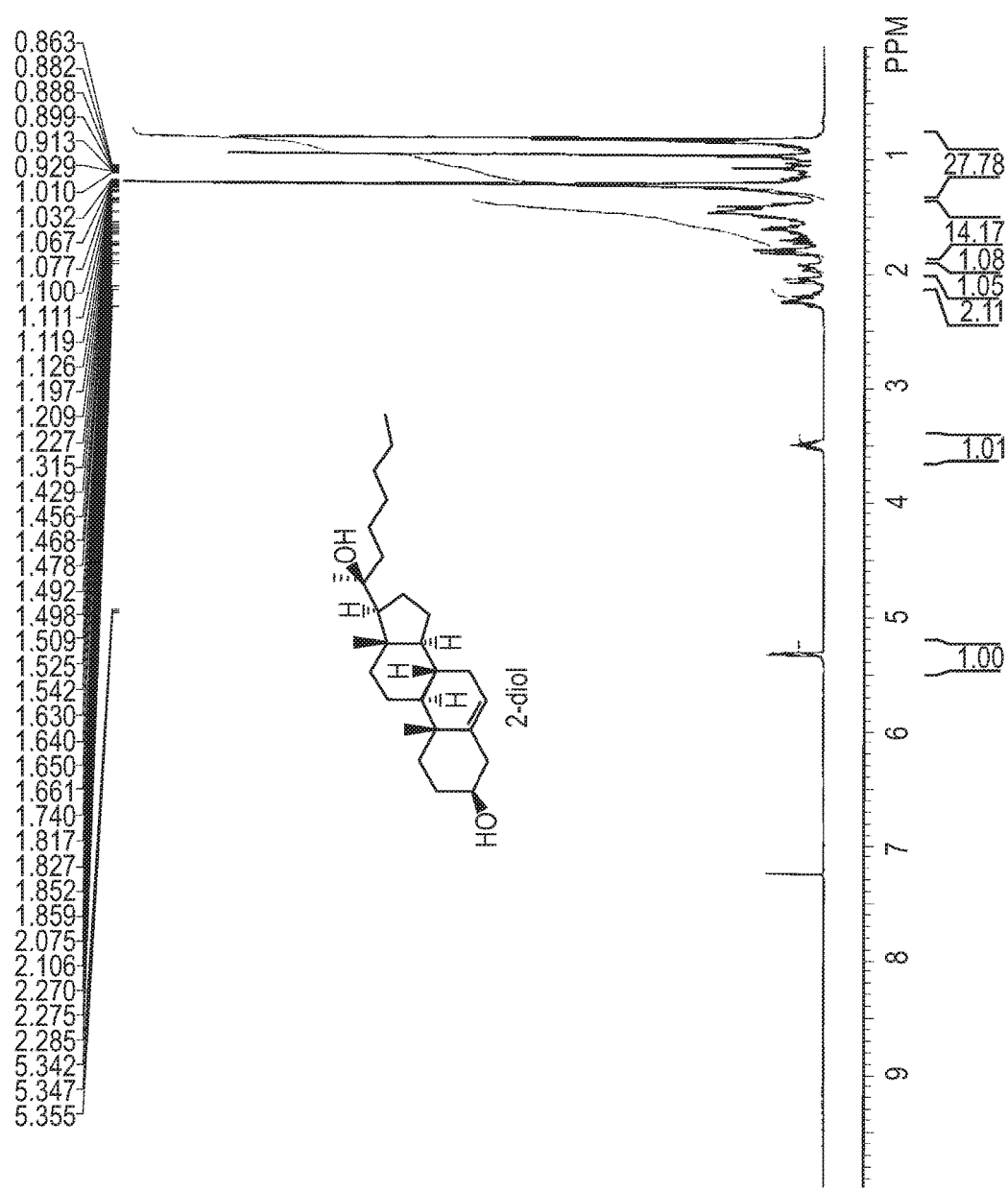
FIG. 6 is a graphic illustration of $^1$H NMR data obtained from the intermediary sterol or diol to synthesize Oxy133.
Figure 7:
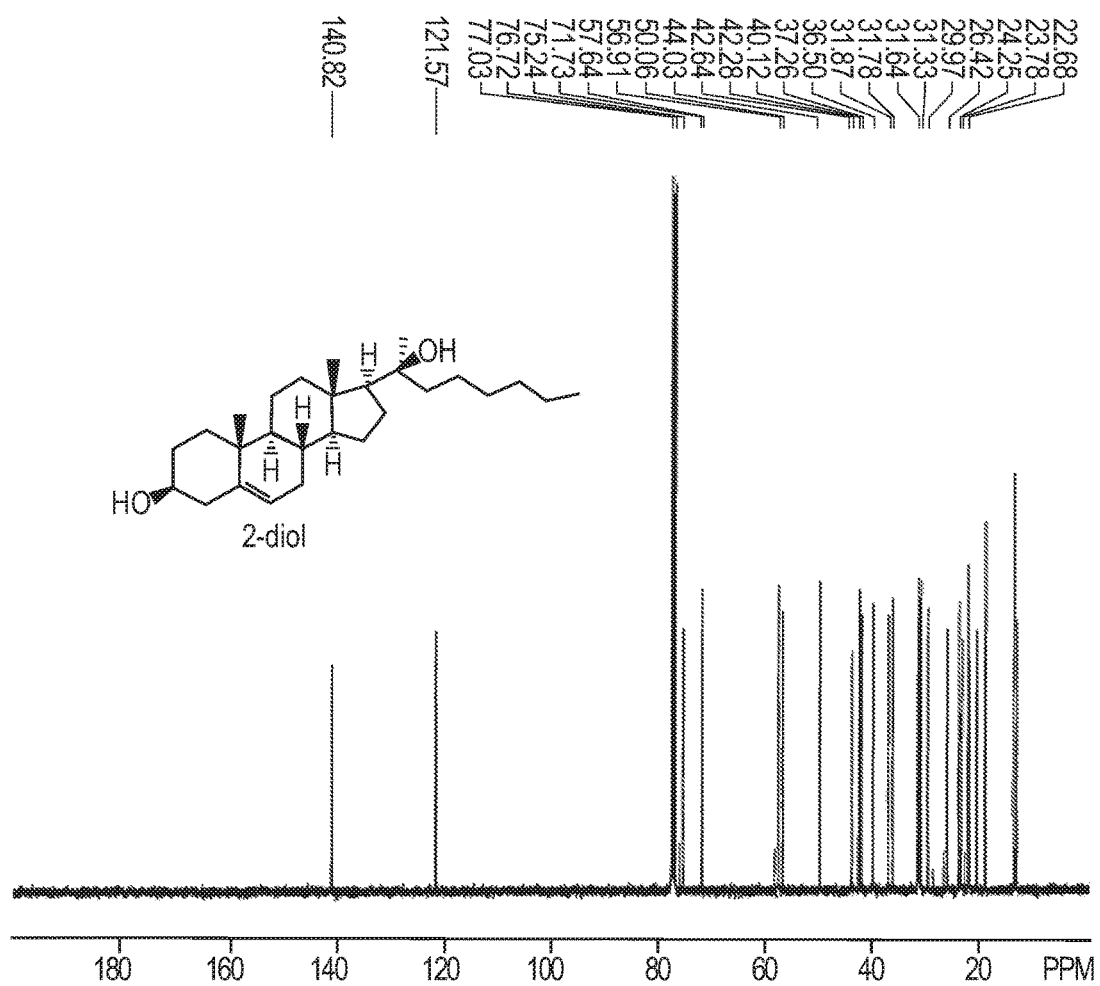
FIG. 7 is a graphic illustration of $^{13}$C NMR data obtained from the intermediary sterol or diol to synthesize Oxy133.

The $^1$H NMR data of the diol in CDCl$_3$ at 400 MHz illustrated the following: δ: 0.8-1.9 (40H), 1.98 (m, 1H), 2.09 (m, 1H), 2.23 (m, 1H), 2.29 (m, 1H), 3.52 (m, 1H), 5.35 (m, 1H) in FIG. 6. The $^{13}$C NMR data of the diol in CDCl$_3$ at 100 MHz in FIG. 7 illustrated the following: d: 13.6, 14.1, 19.4, 20.9, 22.4, 22.6, 23.8, 24.2, 26.4, 30.0, 31.3, 31.6, 31.8, 31.9, 36.5, 37.3, 40.1, 42.3, 42.6, 44.0, 50.1, 56.9, 57.6, 71.7, 75.2, 121.6, 140.8.

The diol created has an IUPAC name of (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Example 2

Preparation from Pregnenolone

Alternatively to Example 1, compound 2 of reaction scheme A above can be prepared from pregnenolone shown below in B utilizing the same procedure as utilized for the conversion of compound 1 to compound 2. In this procedure 10 g of pregnenolone was converted to 7.05 g of compound 2, which accounted for a 55% yield.

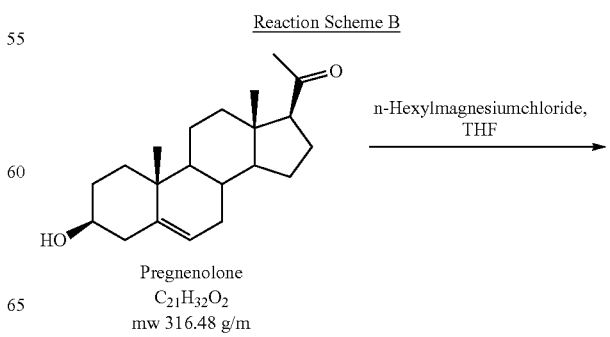

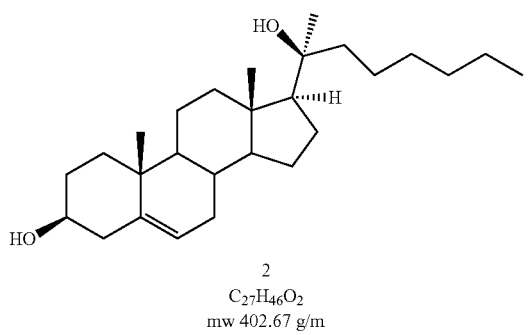

2
C$_{27}$H$_{46}$O$_2$
mw 402.67 g/m

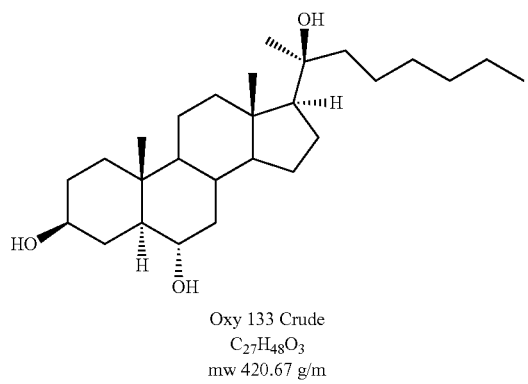

Oxy 133 Crude
C$_{27}$H$_{48}$O$_3$
mw 420.67 g/m 2500 mL of n-hexylmagnesium chloride (2 M, 5 mol) was charged to a reactor and the solution was cooled to −5° C. A solution of pregnenolone acetate in THF was charged to the reactor at a rate which maintained the internal reaction temperature below 1° C. The pregnenolone solution contained 500 g pregnenolone (1.4 mol) in 8 liters THF. After the addition was complete, the mixture was held at 0° C. for 1 hour then allowed to warm to room temperature overnight. The reaction mixture had become a solid, gelatinous mass. 2 liters of additional THF was added followed by 10 ml of glacial acetic acid. The reaction mixture was cooled to 5° C. and quenched by the addition of 350 ml of glacial acetic acid which gave a solution. The reaction mixture was concentrated under reduced pressure to a thick syrup. The compound was dissolved in dichloromethane, washed with water and finally washed with saturated sodium bicarbonate. The organic layer was concentrated under reduced pressure to an amber oil. Mass recovery was about 800 grams. The crude material was utilized as is in the next step.

The diol created has an IUPAC name of (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Example 3

The crude hexyl diol product (800 grams) was dissolved in 8 liters of THF, charged to a reactor, and was cooled to −5° C. 6300 mL of borane-THF complex (1 M, 6.3 moles, 4.5 equivalents) in THF was charged at a rate which maintained the internal reaction temperature below 1° C. Once the addition was complete, the reaction mixture was stirred at 0° C. for 1.5 hours then allowed to warm to room temperature overnight. The reaction is shown below.

The reaction mixture was quenched by addition of a mixture of 10% sodium hydroxide (4750 mL) and 30% hydrogen peroxide (1375 mL). The quench was extremely exothermic and required several hours to complete. The internal temperature was maintained below 10° C. After the addition of the quench volume was complete, the mixture was held cold for 1.5 hours then allowed to warm to room temperature overnight. 8 liters of dichloromethane was then added. The organic layer was isolated and washed with 7 liters of fresh water, and was concentrated under reduced pressure. The product was isolated as a viscous, oily mass which solidified on standing.

The product was dissolved in 4 liters of dichloromethane and was placed onto a silica gel column prepared in dichloromethane. The column was eluted first with 25% ethyl acetate to elute the 7-methyl-7-tridecyl alcohol by-product. Subsequently, the column was eluted with 10% methanol-ethyl acetate to solvate the Oxy133. The collected fractions were combined and concentrated under reduced pressure to a waxy solid. The compound was dissolved in acetone-water mixture (3:1) and concentrated under reduced pressure to remove residual solvents. The resulting crude Oxy133 was utilized in the next step.

Alternatively, the viscous product recovered from the hydroboration/oxidation can be solidified by stirring with heptanes, and the product isolated by filtration. The isolated product is suspended in methylene chloride (7.3 methylene chloride/g solid). The product was isolated by filtration and used as-is in the next step.

Example 4

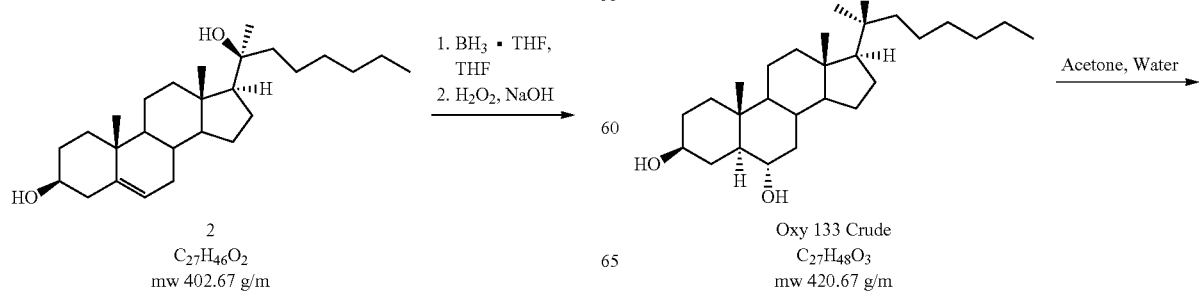

2
C$_{27}$H$_{46}$O$_2$
mw 402.67 g/m

Oxy 133 Crude
C$_{27}$H$_{48}$O$_3$
mw 420.67 g/m

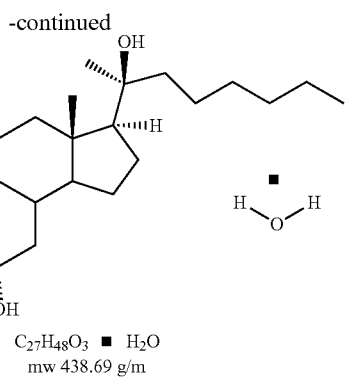

$C_{27}H_{48}O_3 \cdot H_2O$
mw 438.69 g/m

Oxy133 was recrystallized by dissolving 630 grams of crude oxy133 into 1500 ml of a 3:1 acetone/water mixture at reflux, then cooling to room temperature. The crystalline solid was recovered by vacuum filtration and dried to afford 336 g, which was a 28% overall yield from compound 1. The Oxy133 produced was monohydrous, and has an IUPAC name of (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol, monohydrate.

The $^1H$ NMR data of Oxy133 in $CDCl_3$ at 400 MHz illustrated the following: δ: 0.66 (m, 1H), 0.85 (m, 10H), 1.23 (m, 18H), 1.47 (m, 9H), 1.68 (m, 4H), 1.81 (m, 1H), 1.99 (m, 1H), 2.06 (m, 1H), 2.18 (m, 1H), 3.42 (m, 1H), 3.58 (m, 1H). The $^{13}C$ NMR data of Oxy133 in $CDCl_3$ at 400 MHz illustrated the following: d: 13.7, 14.0, 14.3, 21.2, 22.5, 22.8, 23.9, 24.4, 26.6, 30.1, 31.1, 32.1, 32.5, 33.9, 36.5, 37.5, 40.4, 41.7, 43.1, 44.3, 51.9, 53.9, 56.5, 57.9, 69.6, 71.3, 75.4. The infrared spectroscopy data of Oxy133 showed peaks at 3342 cm$^{-1}$, 2929 cm$^{-1}$, 2872 cm$^{-1}$, 2849 cm$^{-1}$. The turbo spray mass spectrometry data of the Oxy133 showed peaks at 438.4 m/z [M+NH$_4$]+, 420.4 m/z (M−H$_2$O+NH$_4$]+, 403.4 m/z [M−H$_2$O+H]+, 385.4 m/z [M−2H$_2$O+H]$^+$. The $^1H$ NMR, $^{13}C$ NMR, IR, and MS of Oxy133 data are shown in FIGS. 2, 3, 4 and 5, respectively.

Example 5

Alternative One-Vessel Procedure from Pregnenolone Acetate 100 mL n-hexylmagnesium chloride (2M in THF, 200 mmol) was charged to a flask and cooled to −10° C. A solution containing 20 g pregnenolone acetate (56 mmol) in 200 ml of anhydrous THF) was added dropwise, while maintaining the internal reaction temperature below −10° C. After the addition was completed, the mixture was stirred for 30 minutes then allowed to warm to room temperature. After 4 hours at room temperature, the mixture had become a gelatinous stirrable mass. The mixture was cooled to 0° C. and 200 mL Borane-THF complex (1M in THF, 200 mmol) was added dropwise, while maintaining the internal temperature below 0° C. Once addition was complete, the resulting solution was allowed to warm to room temperature overnight.

The mixture was cooled to 0° C. and quenched by the slow addition of a mixture of 10% NaOH (190 mL) and 30% $H_2O_2$ (55 mL). Once the quench was complete, the mixture was extracted with MTBE (800 mL total) resulting in an emulsion. Brine was added and the layers were separated. The organic phase was concentrated under reduced pressure to a clear, viscous oil. The oil was further purified utilizing the plug column method previously described.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of making an oxysterol, the method comprising reacting a diol having the formula:

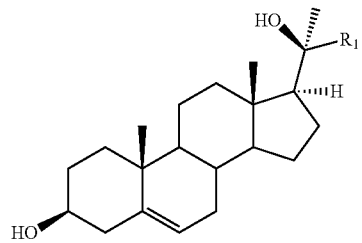

with borane and hydrogen peroxide to form the oxysterol or a pharmaceutically acceptable salt, hydrate or solvate thereof having the formula:

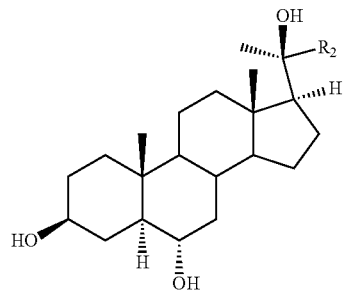

wherein $R_1$ is a straight chain alkyl, and $R_2$ is a straight chain alkyl and the hydrogen peroxide is reacted with the diol at a temperature of less than 15° C.

2. A method of claim 1 wherein $R_1$ and $R_2$ comprise a hexyl group and the diol is (3S,8S,9S,10R,13S,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

3. A method of claim 1 wherein (i) the oxysterol is hydrated, (ii) the borane is reacted with the diol at a temperature of less than 5° C., (iii) the oxysterol is solidified and separated by filtration, or (iv) the oxysterol is (3S,5S,6S,8R,9S,10R,13S,14S,17S) 17-((S)-2-hydroxyoctan-2-yl)-10,13-dimethylhexadecahydro-1H-cyclopenta[a]phenanthrene-3,6-diol.

4. A method of claim 1 wherein the reaction is carried out in a single container to yield the oxysterol having the formula

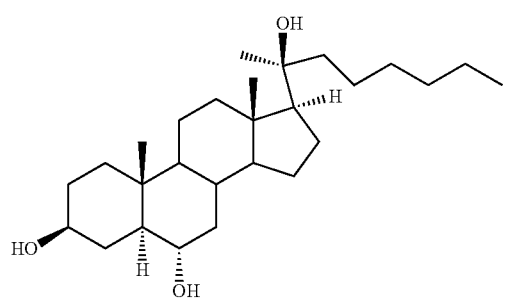 [SMILES: CCCCCC[C@](C)(O)[C@H]1CCC2C3C[C@H](O)[C@H]4C[C@@H](O)CC[C@]4(C)C3CC[C@@]21C]

or a pharmaceutically acceptable salt, hydrate or solvate thereof.

5. A method of claim 4, wherein the reaction vessel is cooled to less than 10° C.

6. A method of claim 4, wherein the reaction vessel is cooled to less than 5° C.

7. A method of claim 4, wherein the reaction vessel is cooled to −5° C.

* * * * *

UNITED STATES PATENT AND TRADEMARK OFFICE
CERTIFICATE OF CORRECTION

PATENT NO. : 10,239,913 B2
APPLICATION NO. : 15/474325
DATED : March 26, 2019
INVENTOR(S) : Harrington et al.

Page 1 of 3

It is certified that error appears in the above-identified patent and that said Letters Patent is hereby corrected as shown below:

In the Specification

In Column 1, Line 51, delete "17S)17-4S)" and insert -- 17S)17-((S) --, therefor.

In Column 2, Line 38, delete "osteoconduction Methods" and insert -- osteoconduction. Methods --, therefor.

In Column 2, Line 65, delete "a organometallic" and insert -- an organometallic --, therefor.

In Column 6, Line 33, delete "ethynyl," and insert -- ethynyl; --, therefor.

In Column 6, Line 36, delete "yl;" and insert -- yl, --, therefor.

In Column 6, Line 66, delete "cycloprop-1-en-1-yl;" and insert -- cycloprop-1-en-1-yl --, therefor.

In Column 7, Line 13, delete "alkenyl" and insert -- alkynyl --, therefor.

In Column 7, Line 30, delete "prop-1-en-1,3-diyl" and insert -- prop-1-en-1,3-diyl, --, therefor.

In Column 7, Line 67, delete ""heteroalkanyl," "heteroalkyldiyl"" and insert -- "heteroalkyldiyl" --, therefor.

In Column 8, Line 8, delete "—P(O)2-," and insert -- —P(O)2—, --, therefor.

In Column 8, Line 9, delete "(O)2-, —SH2-, —S(O)2-," and insert -- (O)2—, —SH2—, —S(O)2—, --, therefor.

In Column 9, Line 33, delete "[1,2]naphthaeno," and insert -- [1,2]naphthaleno, --, therefor.

Signed and Sealed this
Ninth Day of July, 2019

Andrei Iancu
*Director of the United States Patent and Trademark Office*

CERTIFICATE OF CORRECTION (continued)

In Column 11, Line 23, delete "heteroaryleno;" and insert -- heteroaryleno. --, therefor.

In Column 11, Line 26, delete "pyridino)," and insert -- pyridino, --, therefor.

In Column 11, Line 53, delete "indole," and insert -- indolo, --, therefor.

In Column 11, Line 54, delete "isoquinoline," and insert -- isoquinolino, --, therefor.

In Column 12, Line 42, delete "5-13" and insert -- 6-13 --, therefor.

In Column 12, Line 51, delete "—CX3, —CN," and insert -- —CX3, —CF3, —CN, --, therefor.

In Column 12, Line 58, delete "alkanyl, aryl," and insert -- aryl, --, therefor.

In Column 14, Line 8, delete "thereof" and insert -- thereof, --, therefor.

In Column 14, Line 14, delete "terms" and insert -- term --, therefor.

In Column 14, Line 45, delete "microliters" and insert -- microfibers --, therefor.

In Column 16, Line 43, delete "mcg/day," and insert -- mcg/day; --, therefor.

In Column 16, Line 44, delete "ng/days" and insert -- ng/day --, therefor.

In Column 16, Line 54, delete "including," and insert -- including --, therefor.

In Column 17, Line 19, delete "polygalacturonate" and insert -- polygalacturonate, --, therefor.

In Column 17, Line 27, delete "Oxy133" and insert -- Oxy133, --, therefor.

In Column 19, Line 50, delete "3jβ" and insert -- 3β --, therefor.

In Column 20, Line 15, delete "(C2-C20)" and insert -- $(C_2-C_{20})$ --, therefor.

In Column 20, Line 16, delete "(C6-C26)" and insert -- $(C_6-C_{26})$ --, therefor.

In Column 20, Line 16, delete "(C5-C20)" and insert -- $(C_5-C_{20})$ --, therefor.

In Column 20, Line 23, delete "group in" and insert -- group. In --, therefor.

In Column 20, Line 33, delete "as arylaryl," and insert -- an arylaryl, --, therefor.

In Column 20, Line 41, delete "substituent" and insert -- R substituent --, therefor.

In Column 22, Line 45, delete "Pd/C" and insert -- Pd/C, --, therefor.

CERTIFICATE OF CORRECTION (continued)
U.S. Pat. No. 10,239,913 B2

In Column 23, Line 64, delete "$B_2H_6$." and insert -- $B_2H_6$, --, therefor.

In Column 23, Line 67, delete "$IpcBH_2$," and insert -- IpcBH2, --, therefor.

In Column 25, Line 54, delete "Oxy 133" and insert -- Oxy133 --, therefor.

In Column 27, Line 63, delete "1.2 about" and insert -- 1.2 dL/g, about --, therefor.

In Column 27, Line 64, delete "about 1.5" and insert -- about 1.5 dL/g, --, therefor.

In Column 28, Line 3, delete "polyether(amide), PEBA," and insert -- polyether block amide, PEBA, --, therefor.

In Column 28, Line 13, delete "bioabsorbable," and insert -- a bioabsorbable, --, therefor.

In Column 28, Line 18, delete "(PG)," and insert -- (PGA), --, therefor.

In Column 28, Line 34, delete "polylactide" and insert -- polylactide (PLA), --, therefor.

In Column 28, Lines 34-35, delete "D-lactide, L-lactide," and insert -- D-lactide, D,L-lactide, L-lactide, --, therefor.

In Column 28, Line 42, delete "a of about" and insert -- a wt% of about --, therefor.

In Column 28, Line 43, delete "90% 89%," and insert -- 90%, 89%, --, therefor.

In Column 28, Line 44, delete "83%, 87%," and insert -- 83%, 82%, --, therefor.

In Column 29, Line 51, delete "8.25 mL," and insert -- 8.25 mL --, therefor.

In Column 32, Line 46, delete "(7.3" and insert -- (7.3 mL --, therefor.

In Column 33, Line 38, delete "$[M-2H_2O+H]^+$." and insert -- [M-2H2O+H]+. --, therefor.

In Column 33, Line 49, delete "THF)" and insert -- THF --, therefor.

In the Claims

In Column 34, Line 52, in Claim 4, delete "formula" and insert -- formula: --, therefor.